(12) United States Patent
Yun et al.

(10) Patent No.: US 9,359,552 B2
(45) Date of Patent: Jun. 7, 2016

(54) LIQUID CRYSTAL COMPOUND

(71) Applicant: Shijiazhuang Chengzhi Yonghua Display Materials Co. Ltd., Shijiazhuang, Hebei (CN)

(72) Inventors: Guoliang Yun, Shijiazhuang (CN); Gang Wen, Shijiazhuang (CN); Zhian Liang, Shijiazhuang (CN); Ruimao Hua, Shijiazhuang (CN); Kui Wang, Shijiazhuang (CN); Xing Zhang, Shijiazhuang (CN); Zhiguo Xia, Shijiazhuang (CN); Yaohua Han, Shijiazhuang (CN)

(73) Assignee: Shijiazhuang Chengzhi Yonghua Display Materials Co., Ltd., Shijiazhuang (CN)

( * ) Notice: Subject to any disclaimer, the term of this patent is extended or adjusted under 35 U.S.C. 154(b) by 0 days.

(21) Appl. No.: 14/360,008

(22) PCT Filed: Nov. 21, 2012

(86) PCT No.: PCT/CN2012/001568
§ 371 (c)(1),
(2) Date: May 22, 2014

(87) PCT Pub. No.: WO2013/075400
PCT Pub. Date: May 30, 2013

(65) Prior Publication Data
US 2015/0021520 A1  Jan. 22, 2015

(30) Foreign Application Priority Data

Nov. 24, 2011 (CN) .................. 2011 1 0378753 A

(51) Int. Cl.
| | | |
|---|---|---|
| *C09K 19/20* | (2006.01) | |
| *C09K 19/32* | (2006.01) | |
| *C09K 19/44* | (2006.01) | |
| *C09K 19/04* | (2006.01) | |
| *C09K 19/12* | (2006.01) | |
| *C09K 19/30* | (2006.01) | |

(52) U.S. Cl.
CPC ................. *C09K 19/32* (2013.01); *C09K 19/44* (2013.01); *C09K 2019/0466* (2013.01); *C09K 2019/123* (2013.01); *C09K 2019/301* (2013.01); *C09K 2019/3004* (2013.01); *C09K 2019/3021* (2013.01)

(58) Field of Classification Search
CPC ...................................................... C09K 19/44
See application file for complete search history.

(56) References Cited

FOREIGN PATENT DOCUMENTS

CN            102618296 A   *   8/2012

* cited by examiner

*Primary Examiner* — Chanceity Robinson
(74) *Attorney, Agent, or Firm* — Buchanan Ingersoll & Rooney

(57) ABSTRACT

Disclosed is a liquid crystal compound. The compound has a general structural formula as shown by formula I.

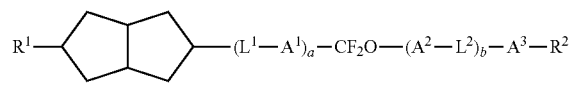

Such a compound has good thermal and UV stability, large positive dielectric anisotropy $\Delta\varepsilon$, and can achieve a low threshold voltage when used in optics, thereby having great significance to the fast response of display devices, and therefore being very suitable for formulating a liquid crystal mixture. A liquid crystal mixture containing such a liquid crystal unit can be applied to various display devices, and is especially suitable for TN-TFT and STN display devices, but can also be used in IPS (in-plane switching) and VA (vertically aligned) display devices.

13 Claims, No Drawings

LIQUID CRYSTAL COMPOUND

RELATED APPLICATION

This application is a national phase application of PCT/CN2012/001568, filed on Nov. 21, 2012, which claims priority to Chinese Patent Application No. 20110378753.2, filed Nov. 24, 2011. The disclosure of which are herein incorporated by reference in their entirety.

TECHNICAL FIELD

The invention relates to the field of liquid crystal compounds and their application, in particular to liquid crystal compounds containing a difluoromethyleneoxy bridge (—$CF_2O$—) and bicyclo[3.3.0]octane ring, their preparation method and application.

TECHNICAL BACKGROUND

At present, the liquid crystal compounds are widely applied in various types of displays, electro-optical devices, sensors and the like, and a large number of liquid crystal compounds have been used in display area, wherein the nematic liquid crystal is most widely used. Nematic liquid crystals have been used in passive TN (twisted nematic), STN matrix display and TFT active matrix system.

The liquid crystal mixtures used in super twisted nematic (STN) mode, often require a large multiplex, a low threshold voltage, and a broad nematic phase range. It is desirable to further improve the properties of liquid crystal monomer used in the mixture for STN mode, especially widening the application range.

Although thin-film transistor technology (TFT-LCD) is maturing, it is still desirable, among other things, to improve the response speed, reduce the drive voltage to decrease the power consumption. It is well-known that liquid crystal materials play an important role to improve the characteristics of the liquid crystal display, as the liquid crystal material, needs to have good chemical and thermal stability and stability of the electric field and electromagnetic radiation. Liquid crystal material for thin-film transistor technology (TFT-LCD) not only requires the stability to heat, UV light, electric field and electromagnetic radiation, but also requires a wide temperature range of a nematic phase, an appropriate optical anisotropy, high resistance, a high voltage holding ratio, and low vapor pressure.

A low rotational viscosity γ1 (even at low temperature), a high dielectric anisotropy (Δ∈) of the liquid crystal mixture has an important significance to improve performance of liquid crystal displays. Therefore, the development of liquid crystal monomer having appropriate physical and chemical properties is the top priority in the future research.

DESCRIPTION OF THE INVENTION

The invention relates to liquid crystal compound, in particular to liquid crystal compounds having a difluoromethyleneoxy bond (—$CF_2O$—) and bicyclo[3.3.0]octane derivatives, and their preparation method and application.

The invention relates to the liquid crystal compound having a difluoromethyleneoxy bond (—$CF_2O$—) and bicycle [3.3.0]octane derivatives expressed by general formula (I):

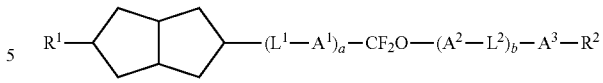

I in which, $R^1$ and $R^2$ are selected from:
H, Cl, F, CN, OCN, $OCF_3$, $CF_3$, $CHF_2$, $OCHF_2$, SCN, NCS, $SF_5$ and alkyl having 1 to 10 carbons, fluorinated alkyl having 1 to 10 carbons, chlorinated alkyl having 1 to 10 carbons, alkoxy having 1 to 10 carbons, fluorinated, alkoxy having 1 to 10 carbons, chlorinated alkoxy having 1 to 10 carbons in which one or more —$CH_2$— are optionally and independently replaced by —CH=CH—, —C≡C—, —COO—, —OOC—, —O— or

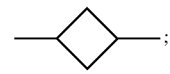

Rings $A^1$, $A^2$ and $A^3$ independently of one another are selected from:

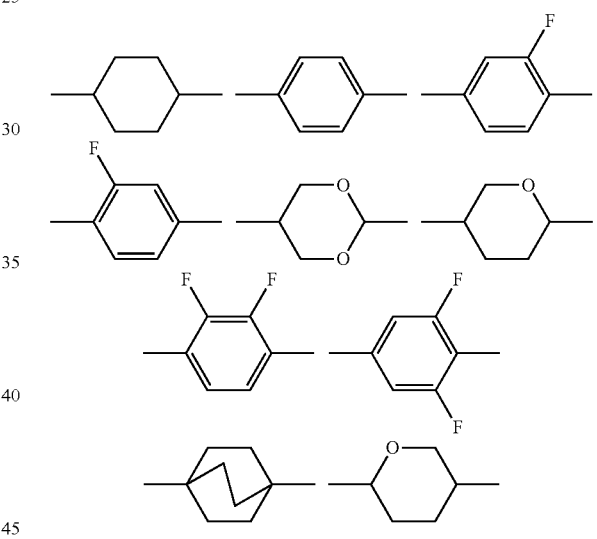

$L^1$ and $L^2$ independently of one another are selected from: a single bond, —CH=CH—, —C≡C—, —COO—, —OOC—, —$CF_2O$—, —$OCH_2$—, —$CH_2O$—, —$OCF_2$—, —$CH_2CH_2$—, —$CF_2CH_2$—, —$CH_2CF_2$—, —$C_2F_4$—, —CF=CF—, —$(CH_2)_4$—;
a and b are 0-3, and a+b≤4.
Said a and b are 2 or 3 at the same time, in the group $A^1$-$L^1$, $A^1$ may be the same or different; $L^1$ may be the same or different: in the group $A^2$-$L^2$, $A^2$ may be the same or different; $L^2$ may be the same or different
Specifically, the compounds according to formula I maybe preferably compounds according to formula Ia,

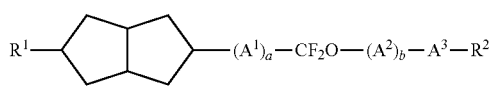

Ia

Wherein $R^1$, $R^2$, $A^1$, $A^2$, $A^3$, a and b are as defined above.
More preferably, the compound of the formula I is at least one compound of formula I1 to I11.

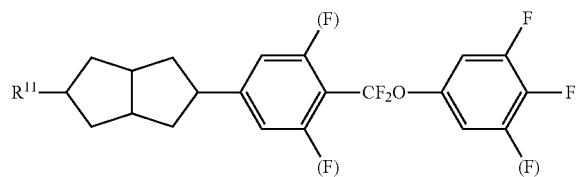
I1
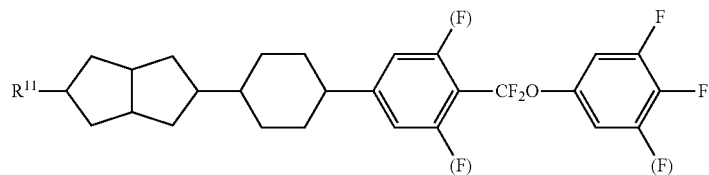
I2
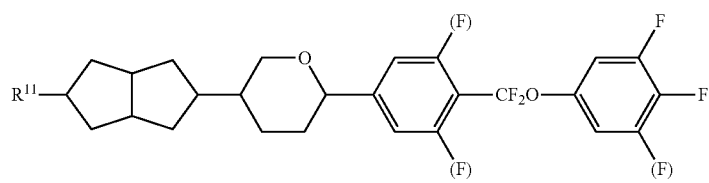
I3
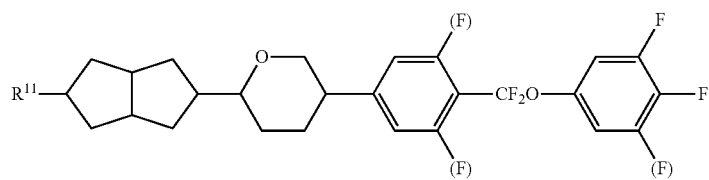
I4
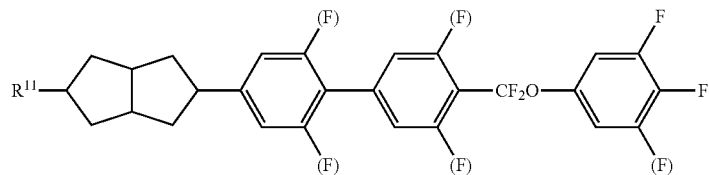
I5
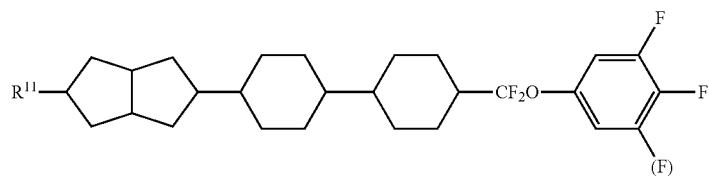
I6
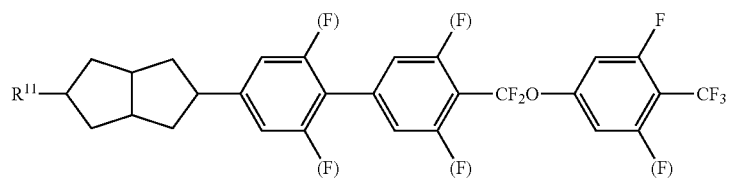
I7
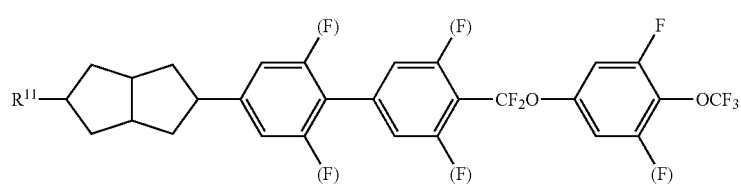
I8

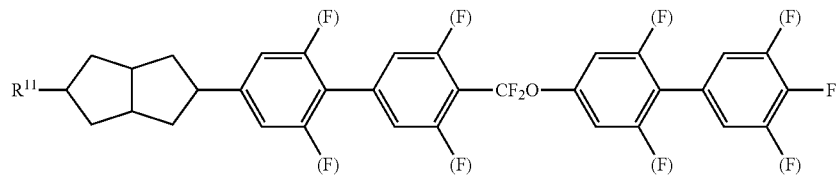
I9

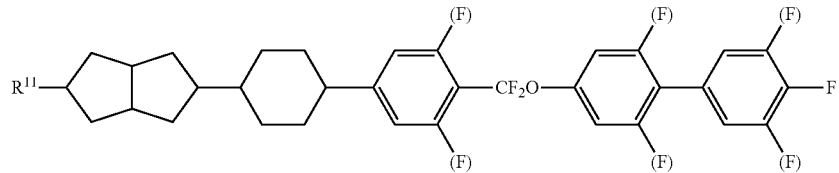
I10

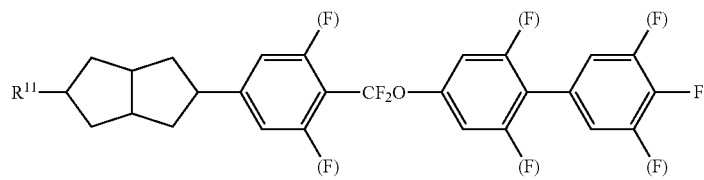
I11

Wherein formula I1 to formula I11, $R^{11}$ selected from H, alkyl having 1 to 10 carbons, alkoxy having 1 to 10 carbons, —(F) represents a fluorine or hydrogen atom on the benzene ring.

Liquid crystal compounds of formula I can be synthesized by the following scheme 1 and 2 (where the synthesis of 7,7-ethylenedioxy-3-bicyclo[3.3.0]octanone according to CN03136662.7, and the introduction of difluoromethyleneoxy (—$CF_2O$—) bond in liquid crystal compound was reported by P. Kirsch in <Modern Fluoroorganic Chemistry>).

Synthetic Route 1: (Preparation of the Compound of Formula I, Wherein $R^1$ is not Hydrogen)

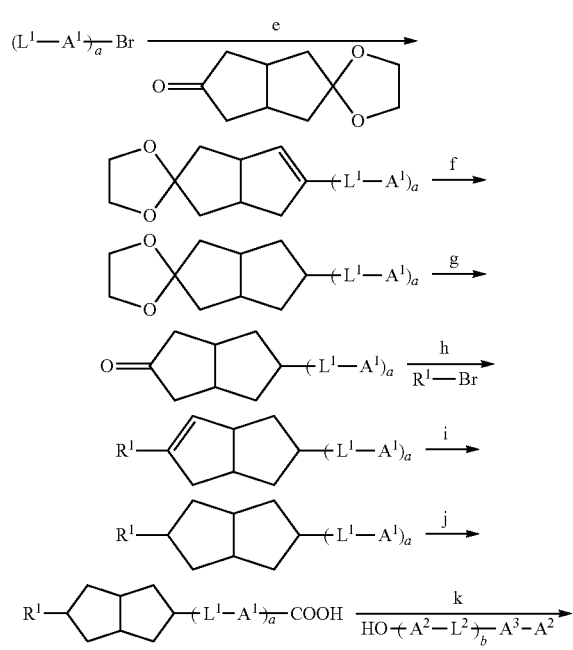

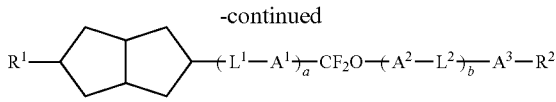

The method comprise the following steps:

1) $(L^1-A^1)_a$-Br, magnesium turnings and anhydrous THF were heated to reflux. Then heated under reflux for additional 1 hour until the magnesium turnings almost completely disappeared, the Grignard reagent solution containing $(L^1-A^1)_a$-MgBr was obtained, then

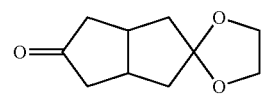 [SMILES: O=C1CC2CC3(CC2C1)OCCO3]

and THF was added dropwise, and refluxed for 2 hours. The reaction solution was cooled to 0° C., then the reaction mixture was poured into a mixture of concentrated hydrochloric acid and ice cold water, and stirred for 2 minutes, the aqueous phase was separated and extracted with ethyl acetate. The combined organic phase was washed twice with saturated brine until neutral pH, and dried over anhydrous sodium sulfate, the product was obtained after removal of solvent. The above obtained product, p-toluenesulfonic acid (catalyst), 2,6-di-tert-butyl-p-cresol (inhibitor), toluene (solvent) and ethylene glycol (solvent) were mixed uniformly, refluxed for 5 hours, and then cooled to room temperature. Ethylene glycol in the lower layer was discarded, the toluene layer was washed successively with saturated sodium bicarbonate solution and deionized water. The toluene layer was dried over anhydrous sodium sulfate for 4 hours, and then filtered. Followed by evaporation of the solvent to give 2) A mixture of

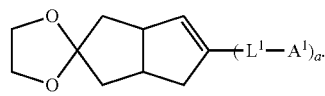

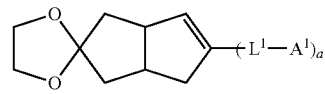

obtained from step 1, isopropyl alcohol (solvent), toluene (solvent), and Raney nickel (catalyst) was hydrogenated at atmospheric pressure until the theoretical amount of hydrogen was consumed to give

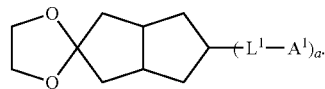

3) A mixture of

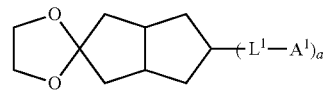

obtained from step 2, formic acid and toluene (solvent) was hydrolyzed to give

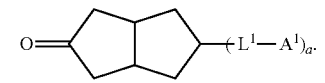

4) $R^1$—Br, magnesium turnings, and anhydrous THF were heated to reflux. When the Grignard reagent solution was obtained,

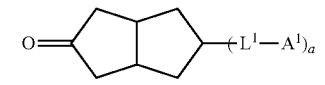

obtained from step 3 and THF was added dropwise, refluxed for 2 hours. The reaction solution was cooled to 0° C., then reaction mixture was poured into a mixture of concentrated hydrochloric acid and ice-water, and stirred for half an hour, the aqueous phase was separated and extracted with toluene. The combined organic phase was washed twice with saturated brine until neutral pH, and dried over anhydrous sodium sulfate, the product was obtained after removal of solvent. The above obtained product, p-toluenesulfonic acid (catalyst), 2,6-di-tert-butyl-p-cresol (inhibitor), toluene (solvent) and ethylene glycol (solvent) were mixed uniformly, refluxed for 5 hours, and then cooled to room temperature. Ethylene glycol in lower layer was discarded, the toluene layer was washed successively with saturated sodium bicarbonate solution and deionized water. The toluene layer was dried over anhydrous sodium sulfate for 4 hours, and then filtered. X The solvent was evaporated to give 5) A mixture of

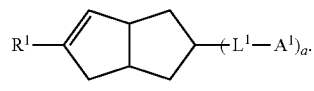

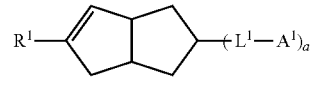

obtained from step 4, isopropyl alcohol (solvent), toluene (solvent), and Raney nickel (catalyst) was hydrogenated at atmospheric pressure until the theoretical amount of hydrogen was consumed to give

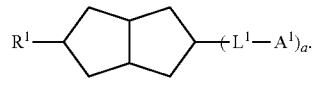

6)

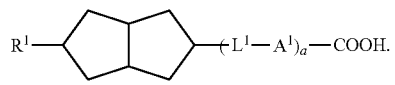

obtained from step 5, and THF (solvent) were placed in a sealed reactor. The air in the sealed reactor is replaced by nitrogen gas, cooled to −70° C. Butyllithium (BuLi) was added dropwise. 20 minutes after the complete addition of BuLi, dry carbon dioxide gas was passed into the reaction mixture to saturation. The reaction continued for 2 hours. The reaction solution was then poured into concentrated hydrochloric acid and water for hydrolysis. The aqueous phase was extracted with ethyl acetate. The combined organic phase was washed with brine until neutral pH, and dried over anhydrous sodium sulfate. After removal of ethyl acetate and recrystallization from isopropanol gave

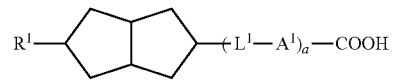

7)

obtained from step 6, toluene (solvent), isooctane (solvent), 1,3-dimercaptopropane were mixed, and was heated to 50° C. At this temperature, trifluoroacetic acid was added in 30 minutes, and the mixture was then heated under reflux to remove water by azeotropic distillation. After the complete removal of water, the reaction mixture was cooled to 90° C., and methyl t-butyl ether was added at 70-90° C. within 45 minutes. The crystals were precipitated after cooling to room temperature, and the crystals were obtained by filtration under nitrogen atmosphere. The crystals obtained above were washed with methyl t-butyl ether, and dried under vacuum.

The above product was then dissolved in dichloromethane, and added dropwise the mixture of HO—(A²-L²)ᵦ-A³-R², triethylamine and dichloromethane (solvent) over 45 min. After stirring at this temperature for an additional hour. NEt₃.3HF was then added in 5 minutes. Bromine dissolved in methylene dichloride was added dropwise to the reaction mixture at −70° C. in one hour, and the reaction mixture was stirred at −70° C. for one hour. When the reaction mixture was warmed up to 0° C., it was poured into 32% aqueous sodium hydroxide and 300 g of ice. The pH value of the mixture was adjusted to 5-8 by 32% aqueous sodium hydroxide. The organic phase was separated, and the aqueous phase was extracted with 80 mL of methylene dichloride. The combined organic phase was then filtered through celite, washed with water. After removal of solvent under reduced pressure, the compound of formula I that R¹ is not hydrogen was obtained.

Synthetic Route 2: (Preparation of the Compound of Formula I, Wherein R¹ is Hydrogen)

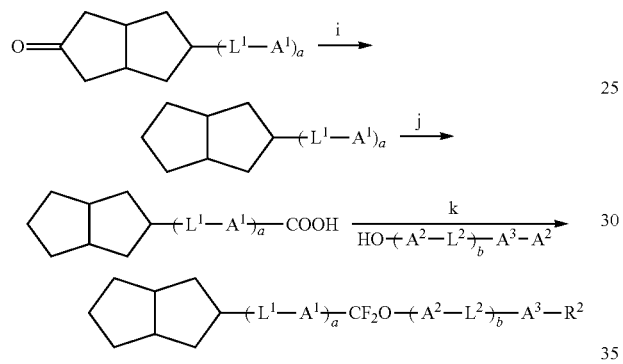

The method comprise the following steps:

1) $(L^1-A^1)_a$-Br, magnesium turnings and anhydrous THF were heated to reflux, and heated under reflux for additional 1 hour until the magnesium turnings disappeared completely, obtaining the Grignard reagent solution containing $(L^1-A^1)_a$-.

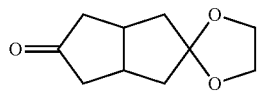 [SMILES: O=C1CC2CC3(CC2C1)OCCO3]

and THF was then added dropwise, refluxed for 2 hours. The reaction solution was cooled to 0° C., then reaction mixture was poured into a mixture of concentrated hydrochloric acid and ice-water, and stirred for 2 minutes, the aqueous phase was separated and extracted with ethyl acetate. The combined organic phase was washed twice with saturated brine until neutral pH, and dried over anhydrous sodium sulfate. The product was obtained after removal of solvent. The above obtained product, p-toluenesulfonic acid (catalyst), 2,6-di-tert-butyl-p-cresol (inhibitor), toluene (solvent) and ethylene glycol (solvent) were mixed uniformly, refluxed for 5 hours, and then cooled to room temperature. Ethylene glycol in lower layer was discarded, the toluene layer was washed successively with saturated sodium bicarbonate solution and deionized water. The toluene layer was dried over anhydrous sodium sulfate for 4 hours, and then filtered, and solvent evaporated to give

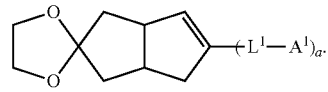

2) A mixture of

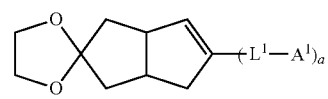

obtained from step 1, isopropyl alcohol (solvent), toluene (solvent), and Raney nickel (catalyst) was hydrogenated at atmospheric pressure until the theoretical amount of hydrogen was consumed to give

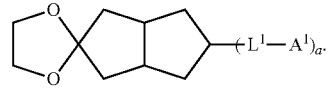

3) A mixture of

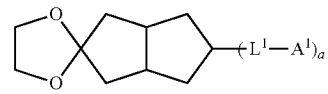

obtained from step 2, methane acid, and toluene (solvent) was hydrolyzed to give

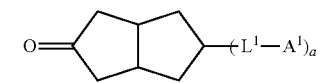

4) A mixture of

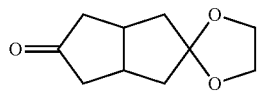 [SMILES: O=C1CC2CC3(CC2C1)OCCO3]

obtained in step 3, 80% hydrazine hydrate, diethylene glycol and potassium hydroxide was heated under reflux for 5 hours. Excess amount of hydrazine hydrate was distilled off, and then the mixture was refluxed in the temperature range of 190-200° C. for additional 3 hours. The reaction mixture was cooled to room temperature to give

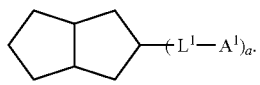

5)

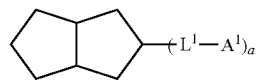

obtained from step 4, and THF (solvent) are placed in a sealed reactor, the air in the sealed reactor is replaced by nitrogen gas, cooling to −70° C., BuLi was added dropwise, 20 minutes after the complete addition of BuLi, dry carbon dioxide gas is passed into the reaction mixture to saturation. The reaction continued for 2 hours at this temperature. The reaction solution was then poured into concentrated hydrochloric acid and water for hydrolysis. The aqueous phase was extracted with ethyl acetate, the combined organic phase was washed with brine until neutral pH, dried over anhydrous sodium sulfate. Removal of ethyl acetate and after recrystallization from isopropanol gave

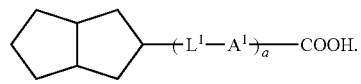

6)

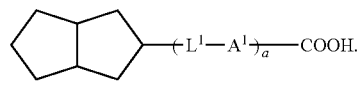

obtained from step 5, toluene (solvent), isooctane (solvent), 1,3-dimercaptopropane were mixed, and was heated to 50° C. At this temperature, trifluoroacetic acid was added in 30 minutes, and the mixture was then heated under reflux to remove the water by azeotropic distillation. The reaction mixture was then cooled to 90° C., and methyl t-butyl ether was added at 70-90° C. within 45 minutes. Crystals were precipitated after cooling to room temperature, and were obtained by filtration under nitrogen atmosphere. The crystals obtained above were washed with methyl t-butyl ether, and dried under vacuum. The above product was then dissolved in dichloromethane, and added dropwise the mixture of HO—(A$^2$-L$^2$)$_b$-A$^3$-R$^2$, triethylamine and dichloromethane (solvent) over 45 min. After stirring at this temperature for additional one hour, NEt$_3$.3HF was added in 5 minutes. Bromine dissolved in methylene dichloride was added dropwise to the reaction mixture at −70° C. in one hour, and the reaction mixture was stirred at −70° C. for additional one hour. The reaction mixture was then warmed up to 0° C., and poured into 32% aqueous sodium hydroxide and 300 g of ice. The pH value of the mixture was adjusted to 5-8 by 32% aqueous sodium hydroxide. The organic phase was separated, and the aqueous phase was extracted with 80 mL of methylene dichloride. The combined organic phase was then filtered through celite, and washed with water. After removal of solvent under reduced pressure, the compound of formula I that R$^1$ is hydrogen was obtained, having the formula

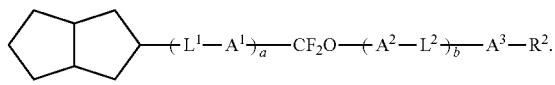

The reaction conditions in the two synthetic routes are as the following:

e: THF, Mg, reflux; toluenesulfonic acid, toluene, reflux.
f: isopropanol, toluene, palladium on carbon, hydrogenation.
g: formic acid, toluene, 30° C.
h: Mg, THF, reflux; p-toluenesulfonic acid, toluene, reflux.
i: isopropanol, toluene, Raney nickel catalyst, hydrogenation.
j: BuLi, CO$_2$, −70° C.
k: propanedithiol, triflate, isooctane, toluene, reflux; methylene chloride, triethylamine, NEt$_3$.3HF, bromine, −70° C.
l: 80% hydrazine hydrate, diethylene glycol, potassium hydroxide.

For the synthetic route 1 and 2, R$^1$, R$^2$, A$^1$, A$^2$, A$^3$, A$^4$, L$^1$, L$^2$, L$^3$, a and b are the same as in the formula I defined above.

Furthermore, at least one of liquid crystal mixture comprises the component A which is represented by the formula I above is also within the claims of the invention.

Said component A comprises 1-5 compounds of formula I, preferably 1-3 compounds of formula I.

Said liquid-crystal mixture further comprises component B:

Said component B comprises one or more compounds selected from the following formula II to XIV

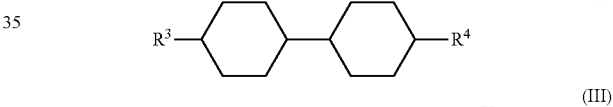

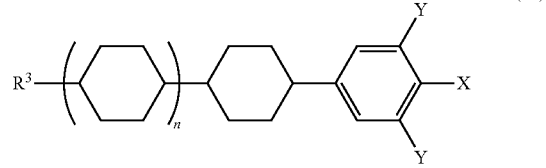

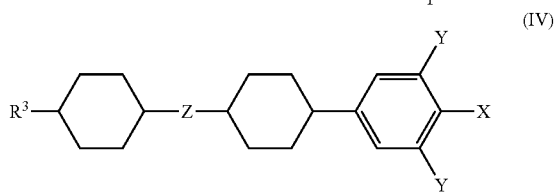

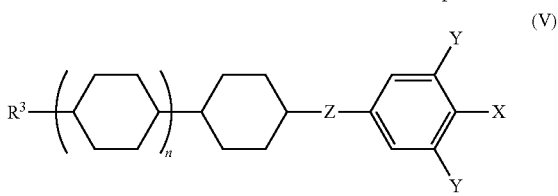

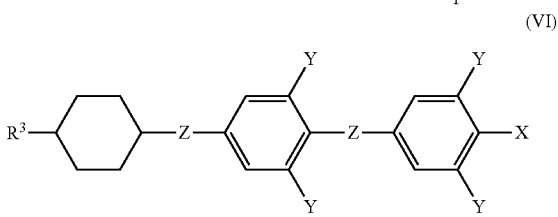

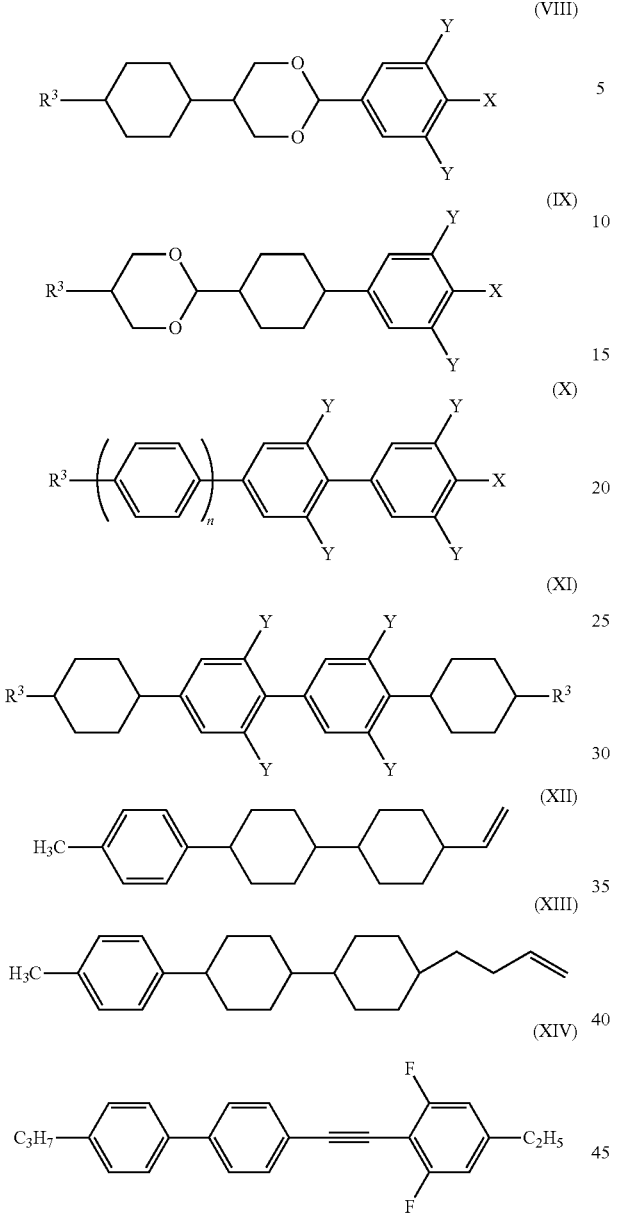

Formula II to XIV, in which $R^3$ and $R^4$ are selected from alkyl having 1 to 9 carbons, fluorinated alkyl having 1 to 9 carbons, alkoxy having 1 to 9 carbons, alkenyl having 1 to 9 carbons, alkenyloxy having 1 to 9 carbons.

Z is selected from a single bond, —CH=CH—, —C≡C—, —COO—, —OOC—, —CF$_2$O—, —CH$_2$O—, —OCF$_2$—, —CH$_2$CH$_2$—, —CF$_2$CH$_2$—, —C$_2$F$_4$— or —(CH$_2$)$_4$—.

Y is H or F;

X is F, Cl, halogenated alkyl having 1 to 9 carbons, halogenated alkenyl having 1 to 9 carbons, alkenyl having 1 to 9 carbons, halogenated alkoxy having 1 to 9 carbons, halogenated alkenyloxy having 1 to 9 carbons or alkyl having 1 to 9 carbons;

n is 0 or 1.

Said component B comprises one or more compounds selected from the following formula:

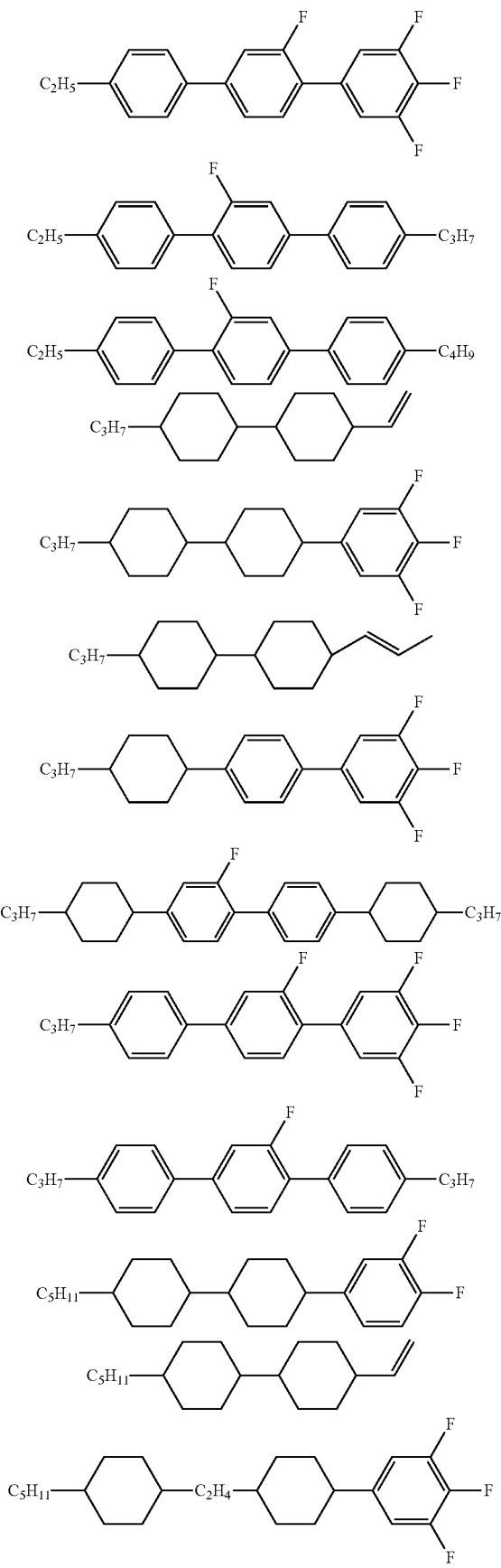

-continued

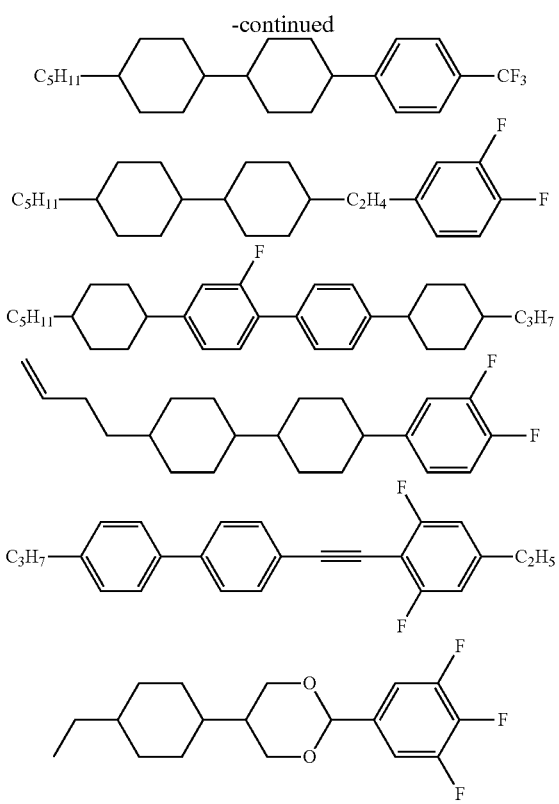

For the liquid crystal mixture, the mass ratio of component A and component B is of 1-70:100, preferably 2-40:100, more preferably 13:100.

Specifically, the liquid crystal mixture consists of components A and B, mass ratio of component A and component B is of 1-70:100, preferably 2-40:100, more preferably 13:100.

Specifically, said liquid crystal mixture is mixture M1 or mixture M2:

The mixture a consists of the components A and B:

Said component A is

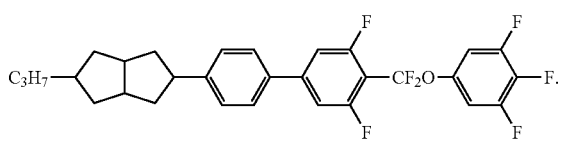

Said component B consists of the following compounds in which the compounds have the following mass ratio:

| compound | mass ratio |
|---|---|
| C₃H₇—◯—◯—⫽ | 21 |
| C₅H₁₁—◯—◯—⫽ | 6 |
| H₃C—◯—◯—◯—⫽ | 14 |
| C₃H₇—◯—◯—◯(F,F,F) | 6 |
| C₃H₇—◯—◯—◯(F,F,F) | 16 |
| H₃C—◯—◯—◯—CH₂CH=CH₂ | 10 |

| compound | mass ratio |
|---|---|
| 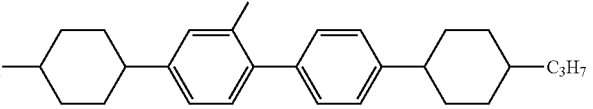 | 4.5 |
| 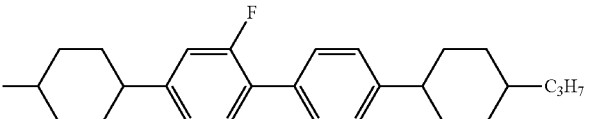 | 4.5 |
| 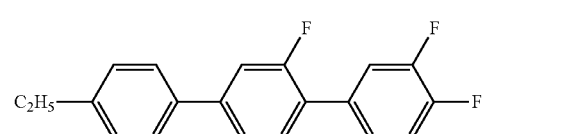 | 9 |
| 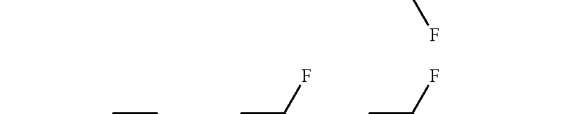 | 9 |
For the mixture a, the mass ratio of component A and component B is 13:100. The mixture b consists of the components A and B, and the component A consists of
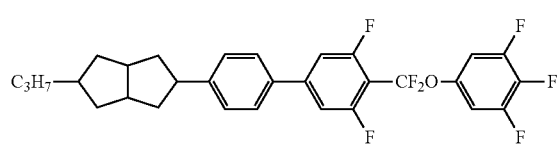
-continued
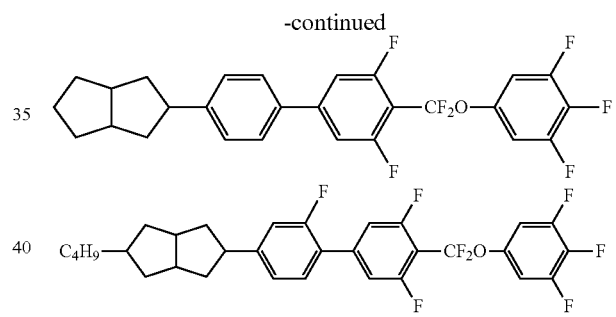
Said component B consists of the following compounds in which the compounds have the following mass ratio:
| compound | mass ratio |
|---|---|
| 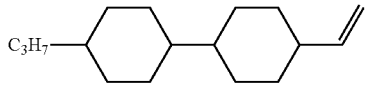 | 41 |
| 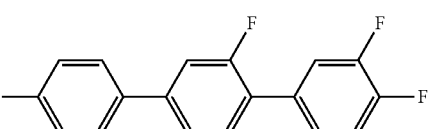 | 10 |
|  | 13 |

-continued

| compound | mass ratio |
|---|---|
|  | 4 |
| 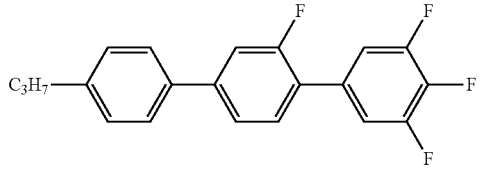 | 10 |
| 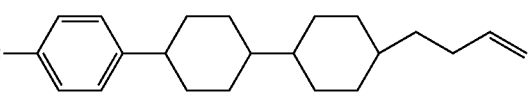 | 10 |
| 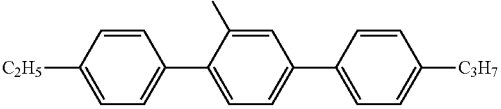 | 6 |
| 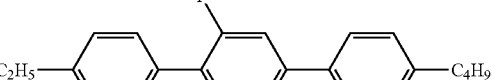 | 6 |

For the mixture b, the mass ratio of

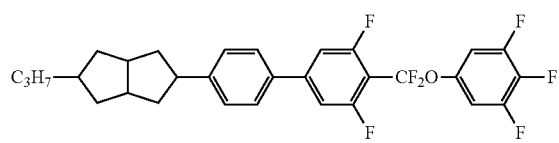

and the component B is 6:100. The mass ratio of

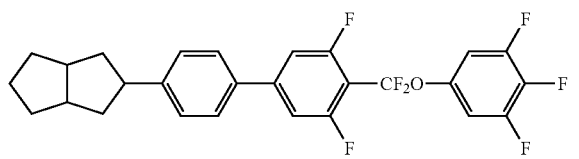

and the component B is 3:100. The mass ratio of

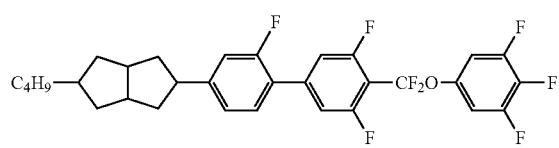

and the component B is 4:100.

Obviously, because bicyclo[3.3.0]octane structure is chemically stable, it is difficult to be hydrolyzed, oxidized or broken, such a liquid crystal mixture has a good stability against heat and ultraviolet light.

THE EXAMPLES OF THE PRESENT INVENTION

The following examples illustrate the present invention without limiting it in any way. Within this application, GC is gas chromatography purity, HPLC is HPLC purity, MP is melting point, CP is clearing point, MS is mass spectrometry, $^1$H-NMR is nuclear magnetic resonance spectrum, $\Delta\in$ is dielectric anisotropy, $\Delta n$ is Optical anisotropy, $V_{th}$ is threshold voltage. The detected temperature is 25° C.

Example 1

Preparation of

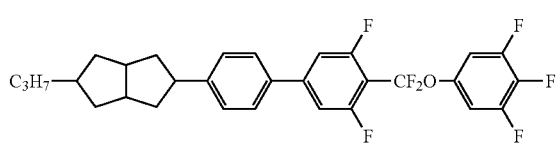

Step 1: Preparation of

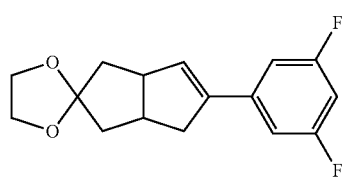

(1-a)

30.0 g of magnesium turnings (reactants) and 250 mL of anhydrous THF (solvent) was added into a 3-L three-necked flask equipped with a 500 mL dropping funnel. 220 g of 3,5-difluoro-bromobenzene (reactants) (99.7%) and 300 mL of anhydrous tetrahydrofuran (THF, solvent) was added to the dropping funnel, first 15 mL of this solution in the dropping funnel was added dropwise into the three-necked flask, and heated to reflux. Then slowly added the remaining solution dropwise, keeping a slight reflux. Following the complete addition of the 3,5-difluoro-bromobenzene/THF solution, the reaction mixture was then heated under reflux for additional 1 hour, until the magnesium turnings almost completely disappeared. 182 g of 7,7-ethylenedioxy-3-bicyclo[3.3.0]octane (reactants) and 400 mL of THF (solvent) was then added dropwise, refluxed for 2 hours. The reaction solution was cooled to 0° C., then poured into a mixture of 110 mL of concentrated hydrochloric acid (reactants) and 500 g of ice-water (solvent), and stirred for 2 minutes. The aqueous phase was separated and extracted with 100 mL of ethyl acetate (solvent). The combined organic phase was washed twice with saturated brine until neutral pH, and dried over anhydrous sodium sulfate. A light yellow solid was obtained after removal of solvent.

20.0 g of p-toluenesulfonic acid (catalyst), 1.0 g of 2,6-di-tert-butyl-p-cresol (inhibitor), 1000 mL of toluene (solvent), 200 mL of ethylene glycol (solvent) and the above obtained light yellow solid were placed in 2-L three-necked bottle, refluxed for 5 hours, and then cooled to room temperature. Ethylene glycol in lower layer was discarded, the toluene layer was washed successively with 200 mL of saturated sodium bicarbonate solution and 500 mL of deionized water (solvent). The toluene layer was dried over anhydrous sodium sulfate (desiccant) for 4 hours, and then filtered off the solid, evaporated the solvent to give a crude product. The crude product was recrystallized twice with two volumes of isopropanol and petroleum ether (1:1). 139 g of 1-a was obtained as white crystals.

Step 2: Preparation of

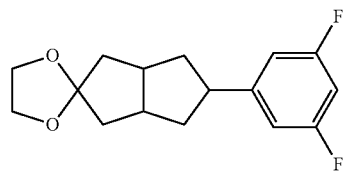

(1-b)

A mixture of 139 g of (1-a) (reactant), 260 mL of isopropyl alcohol (solvent), 300 mL of toluene (solvent), and 50 g of Raney nickel (catalyst) (an amount of 1-20% by weight of the substrate) in 5-L single neck flask was hydrogenated at atmospheric pressure for 5 hours until the theoretical amount of hydrogen was consumed. After Raney nickel catalyst was removed by filtration, the solvent was concentrated to give 139 g of 1-b as slightly yellow of solid (1-b). mp: 55.5° C.; purity by GC: 99.5%.

Step 3: Preparation of

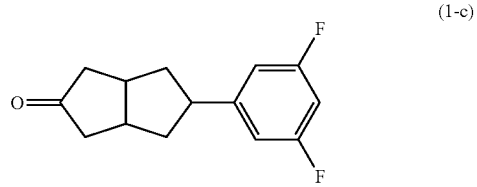 [SMILES: O=C1CC2CC(c3cc(F)cc(F)c3)CC2C1]

(1-c)

40 g of 3,3-ethylenedioxy-7-(3',4'-difluorophenyl)-bicyclo[3.3.0]octane (1-b) obtained in step 2 (reactants), 500 mL of 88% formic acid (reactants), 300 mL of toluene (solvent) were added into 1-L one-necked flask, stirred at room temperature for hydrolysis for 12 hours, the toluene layer was then washed with water to neutral pH, dried over anhydrous sodium sulfate for 4 hours. After removal of solid by filtration, the solvent was removed by distillation under reduced pressure to afford 32 g of 3-oxo-7-(3',5'-difluorophenyl)-bicyclo[3.3.0]octane (1-c). Purity by GC: 99.0%.

Step 4: Preparation of

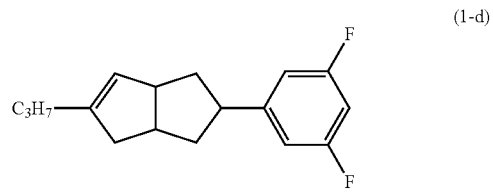

(1-d)

8.0 g of magnesium turnings (reactants) and 300 mL of anhydrous THF (solvent) were placed in a 1-L three-neck flask, and 37 g of bromopropane (analytical reagent) (reactants) was added dropwise to obtain Grignard reagent, and then 32 g of compound 3-oxo-7-(3',5'-difluorophenyl)-bicyclo[3.3.0]octane (1-c) (reactants) obtained in Step 3 was added at room temperature. The reaction mixture was refluxed for two hours, and then poured into a solution of 72 mL of hydrochloric acid (6M) for hydrolysis for 30 min at room temperature. 150 mL of toluene (solvent) was then added, and the toluene layer was washed with water to neutral pH, and removed by evaporation under reduced pressure to give an alcohol intermediate.

5.0 g of p-toluenesulfonic acid (catalyst), 0.5 g of 2,6-di-tert-butyl-p-cresol (inhibitor), 200 mL of toluene (solvent), 50 mL of ethylene glycol (solvent) and the above obtained alcohol intermediate were placed in 500 mL three-necked flask, and was refluxed for 5 hours. After the reaction mixture was cooled to room temperature, ethylene glycol in lower layer was discarded, the toluene layer was washed successively with 50 mL of saturated sodium bicarbonate solution and 50 mL of deionized water. The toluene layer was dried over anhydrous sodium sulfate for 4 hours, and then filtered off the solid, evaporated the solvent to give a crude product. The crude product was recrystallized twice with two volumes of isopropanol and petroleum ether (1:1), and 21 g of 1-d was obtained as white crystals.

Step 5: Preparation of

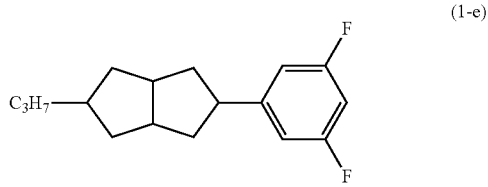
(1-e)

21 g (1-d) obtained in the step 4, 150 mL of isopropyl alcohol (solvent), 50 g of Raney nickel (catalyst) (an amount of 1-20% by weight of the substrate) in 1-L single neck flask was hydrogenated at atmospheric pressure for 5 hours until the theoretical amount of hydrogen was absorbed, After Raney nickel catalyst removed by filtration, the solvent was concentrated to afford 21 g of (1-e) as slightly yellow solid. Purity by GC: 99.1%.

Step 6: Preparation of

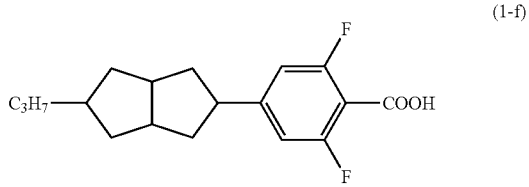
(1-f)

21 g of (1-e) (reactants) obtained from step 5, 150 mL of THF (solvent) are placed in a 500 mL of sealed reactor, the air in the sealed reactor is replaced by nitrogen gas, cooled to −70° C., 0.1 mL of 2.5M BuLi (reactants) was added dropwise. After 20 minutes, dry carbon dioxide (reactants) gas is passed into the reaction mixture to saturation. The reaction continued for 2 hours. The reaction solution was then poured into 20 mL of concentrated hydrochloric acid (reactants) and 100 mL of water (solvent) for hydrolysis. The aqueous phase was extracted with 50 mL of ethyl acetate (solvent), the combined organic phase was washed with brine until neutral pH, dried over anhydrous sodium sulfate. Removal of ethyl acetate gave a pale yellow solid, and after recrystallization from isopropanol gave 18 g of (1-f) as white crystals.

Step 7: Preparation of

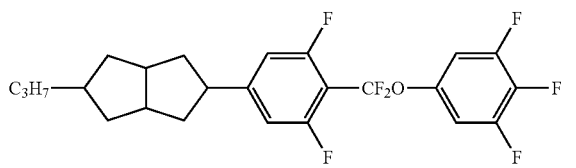
(1-g)

30.8 g of (1-f) (reactants), 30 mL of toluene (solvent), 30 mL of isooctane (solvent), 14 g of 1,3-dimercaptopropane (reactants) were placed into a 250-mL three-necked flask, and was heated to 50° C. At this temperature, 19.2 g of trifluoroacetic acid (reactants) was added in 30 minutes, and the mixture was then heated under reflux to remove water by azeotropic distillation, The reaction mixture was then cooled to 90° C., and 100 mL of methyl t-butyl ether (solvent) was added at 70-90° C. within 45 minutes. Crystals were precipitated after cooling to room temperature, and the crystals were obtained by filtration under nitrogen atmosphere, and washed with methyl t-butyl ether (solvent) (25 mL×4), dried under reduced pressure to afford 45 g of dithiane trifluoromethanesulfonate for next reaction.

A mixture of 14.8 g of 3,4,5-trifluorophenol (reactants), 10.8 g of triethylamine (reactants) and 130 mL of dichloromethane (solvent) in a 500-mL three-necked flask was cooled to −70° C., and 45 g of dithiane trifluoromethanesulfonate dissolved in 120 mL of dichloromethane (solvent) was added dropwise over 45 min. After stirring at this temperature for additional one hour, $NEt_3.3HF$ (reactants) was added in 5 minutes. 72 g of bromine (reactants) dissolved in 30 mL of methylene dichloride (solvent) was added dropwise to the reaction mixture at −70° C. in one hour, and the reaction mixture was stirred at −70° C. for additional one hour. When the reaction mixture was warmed up to 0° C., it was poured into 160 mL of 32% aqueous sodium hydroxide (reactants) and 300 g of ice. The pH value of the mixture was adjusted to 5-8 by about 45 g 32% aqueous sodium hydroxide. The organic phase was separated, and the aqueous phase was extracted with 80 mL of methylene dichloride (solvent). The combined organic phase was then filtered through 4 g celite, washed with water. After removal of solvent under reduced pressure, the crude product was purified by column chromatography, and recrystallized from petroleum ether. 23 g of 1-g was obtained. Purity by GC: 99.9%.

MS: (m/z %) 460 ($M^+$, 0.03), 313 (100), 189 (15.8), 163 (20.3);

$^1$H-NMR: 6.93-6.97 (t, 2H), 6.83-6.86 (d, 2H), 3.06-3.15 (m, 1H), 2.51-2.54 (m, 2H), 2.24-2.28 (m, 2H), 2.06-2.10 (m, 2H), 1.93-1.97 (m, 1H), 1.32-1.33 (m, 6H), 0.89-0.91 (m, 5H);

mp: 41.5° C.

Based on the above data, the structure of the obtained product is the expected compound 1-g, which shows Δ∈: 17.6 (20° C., 1000 Hz).

Example 2

Preparation of

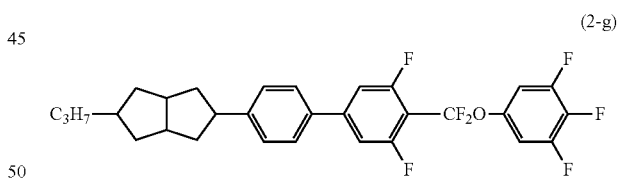
(2-g)

Example 2 is prepared similarly to Example 1. 3,5-difluoro-bromobenzene was replaced by the 3',5'-difluoro-4-bromo-biphenyl. In each step, the structures of the intermediate are shown as follows:

step 1:

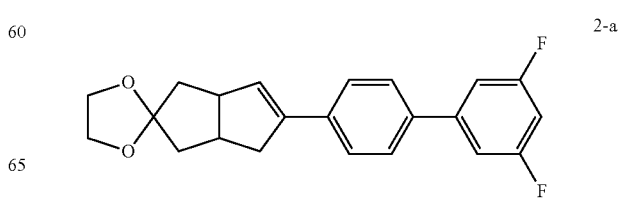
2-a step 2:

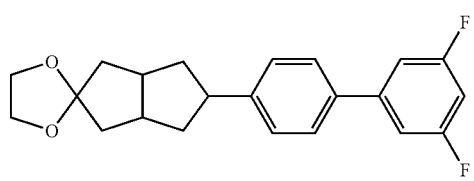
2-b step 3:

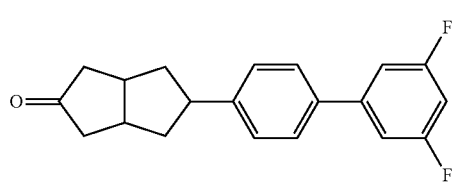
2-c step 4:

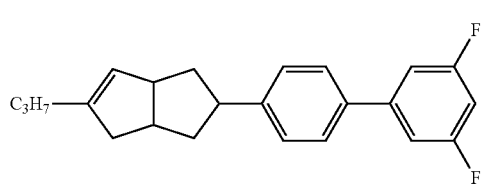
2-d step 5:

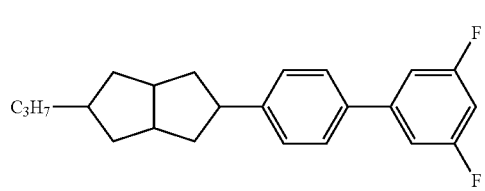
2-e step 6:

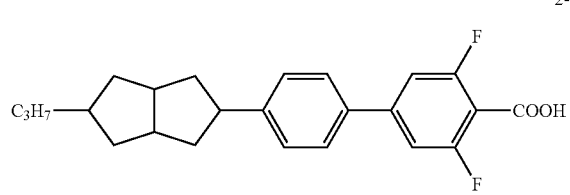
2-f step 7:

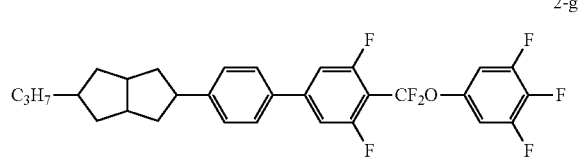
2-g

GC: 99.93%;

MS: (m/z %) 536 (M+, 0.7), 389 (100), 265 (9.9), 252 (3.4), 239 (2.7);

$^1$H-NMR: 7.47-7.50 (d, 2H), 7.33-7.36 (d, 2H), 7.18-7.25 (d, 2H), 6.96-7.01 (t, 2H), 3.11-3.23 (m, 1H), 2.54-2.56 (m, 2H), 2.29-2.33 (m, 2H), 2.04-2.12 (m, H), 1.90-0.99 (m, 1H), 1.33-1.35 (m, 6H), 0.88-0.92 (m, 5H);

mp 66.5° C.

Based on the above data, the structure of the obtained product is the expected compound 2-g, which shows $\Delta\varepsilon$: 14.3 (20° C., 1000 Hz); $\Delta$n: 0.109 (20° C., 589 nm).

Example 3

Preparation of

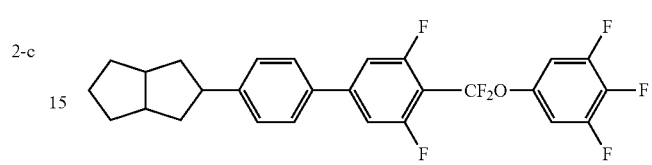

Step 1: Preparation of

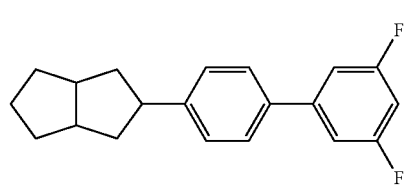
(3-a)

A mixture of 31.2 g of (2-c) obtained in Example 2 (reactants), 60 mL of 80% hydrazine hydrate (reactants), 200 mL diethylene glycol (solvent) and 20 g of potassium hydroxide (catalyst) in a 500-mL of three-necked flask was heated under reflux for 5 hours, and the excess amount of hydrazine hydrate was distilled off, and then the mixture was refluxed in the temperature range of 190-200° C. for additional 3 hours. The reaction mixture was then poured into 500 mL of water, when it was cooled to room temperature. The mixture was extracted with petroleum ether (90-120, 100 mL×2, solvent), and petroleum ether (solvent) was washed with water to neutral pH. The petroleum ether (solvent) was distilled off under reduced pressure, the residue was recrystallized with petroleum ether (solvent) to give 17.8 g of 3-a as pale yellow solid. Purity by GC: 99.1%.

Step 2: Preparation of

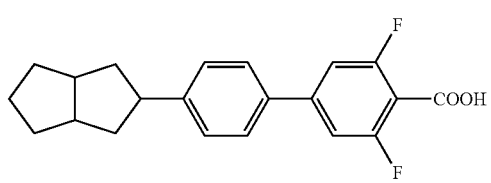
(3-b)

18 g of 3-b was prepared similarly to step 6 in example 1, when 1-e was replaced by 27.3 g of 3-a. Purity by HPLC: 98.8%.

Step 3: Preparation of

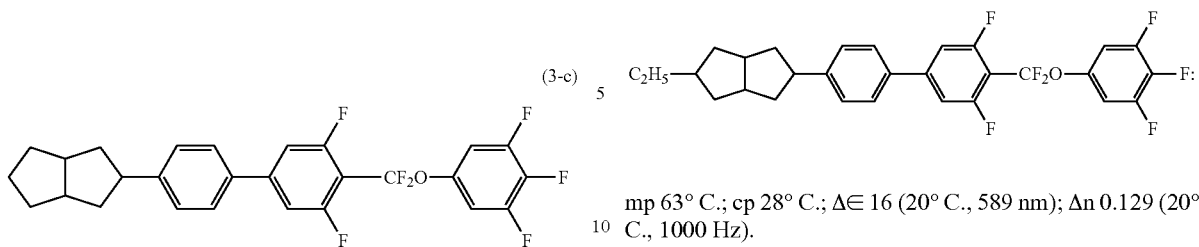
(3-c)

17 g of 3-c was prepared similarly to step 7 in example 1, when 1-f was replaced by 34.2 g of 3-b. Purity by GC: 99.92%; mp 78° C.; cp 6° C.; Δ∈ 18 (20° C., 589 nm); Δn 0.121 (20° C., 1000 Hz).

Example 4-29

The following liquid crystal compounds of formula I were obtained using the method described in examples 1-3 by replacing only the different corresponding reactants.

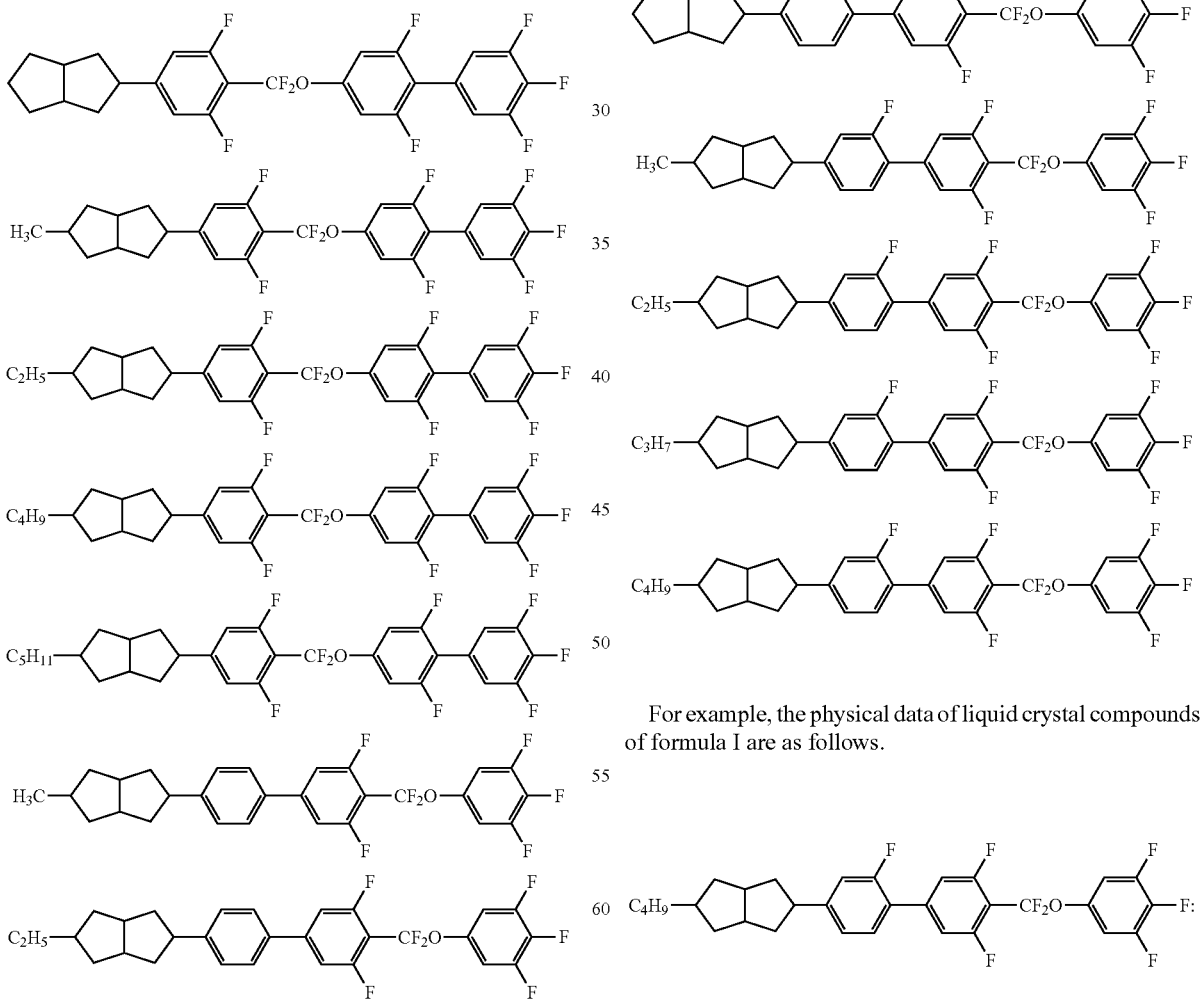

For example, the physical data of liquid crystal compounds of formula I are as follows.

mp 63° C.; cp 28° C.; Δ∈ 16 (20° C., 589 nm); Δn 0.129 (20° C., 1000 Hz).

For example, the physical data of liquid crystal compounds of formula I are as follows.

mp 67° C.; cp 28° C.; Δ∈ 15 (20° C., 589 nm); Δn 0.094 (20° C., 1000 Hz).

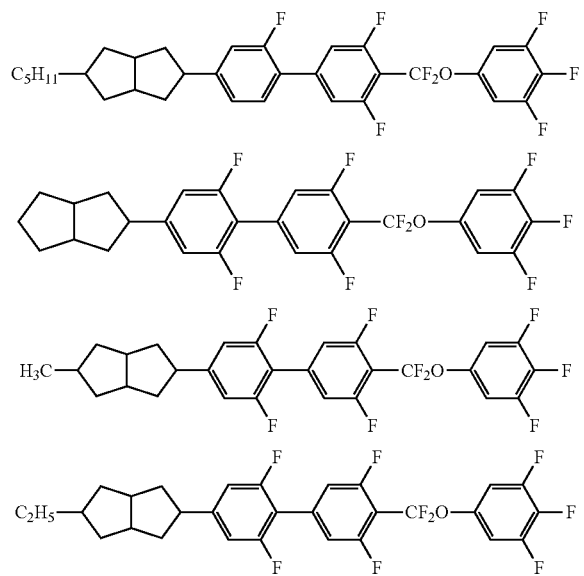

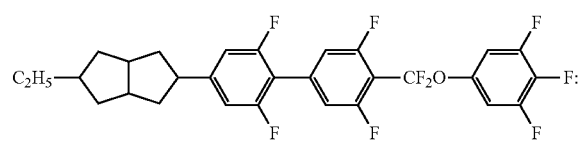

For example, the physical data of liquid crystal compounds of formula I are as follows.

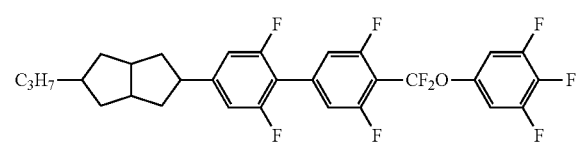

mp 70° C.; cp −12° C.; Δ∈ 17 (20° C., 589 nm); Δn 0.080 (20° C., 1000 Hz).

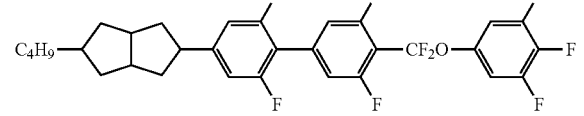

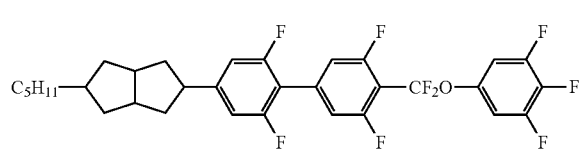

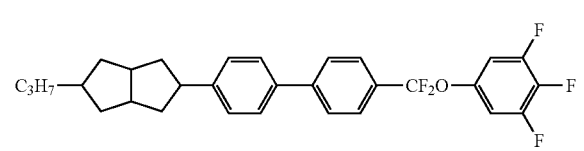

For example, the physical data of liquid crystal compounds of formula I are as follows.

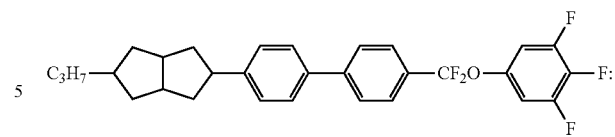

mp 86° C.; cp 76° C.; Δ∈ 10 (20° C., 589 nm); Δn 0.127 (20° C., 1000 Hz).

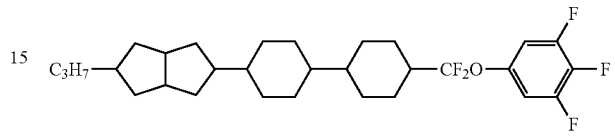

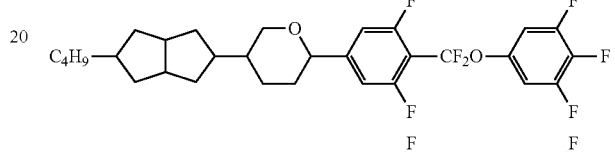

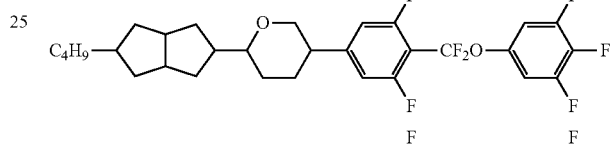

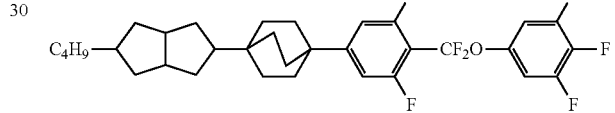

The nuclear magnetic test results and the physical data of liquid crystal compounds 4-29 of formula I is similar to examples 1-3 that described above.

The liquid crystal compounds of formula I as follows were prepared similarly to example 1, when reactants were replaced with corresponding substituents. Additional liquid crystal compounds of formula I were prepared similarly to example 3, when reactants were replaced with corresponding substituents.

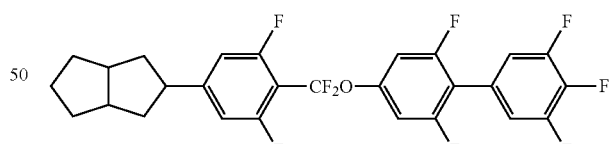

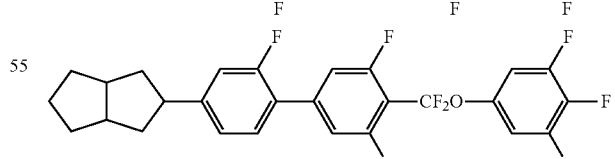

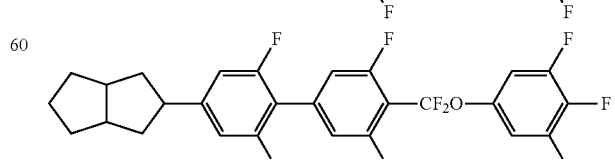

Based on the physical data of the above examples 4-29, the liquid crystalline compounds of formula I have good thermal and UV stability, moderate optical anisotropy (Δn), large dielectric anisotropy (Δε). They also have a wide range of nematic phase temperature and a low rotational viscosity γ1, resulting in a low threshold voltage when they are used in LC display devices with fast response time, therefore being very suitable for formulating a liquid crystal mixture.

Example 30

Liquid Crystal Mixture

The component A and component B were mixed in a mass ratio of 100:13 to obtain the liquid crystal mixture. In which the component A consists of the following compounds, which have the following mass ratio:

| compound | mass ratio |
|---|---|
| 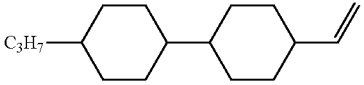 | 21 |
| 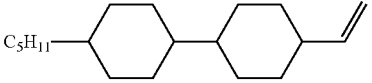 | 6 |
|  | 14 |
| 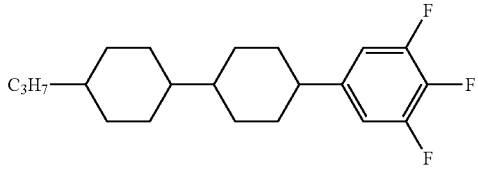 | 6 |
| 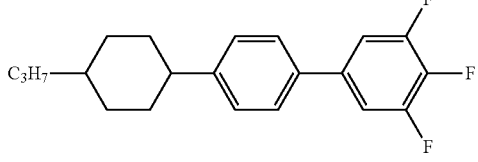 | 16 |
| 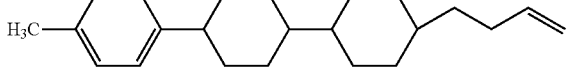 | 10 |
| 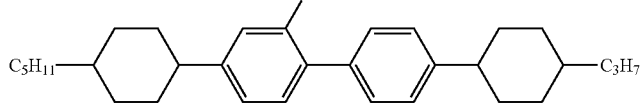 | 4.5 |
| 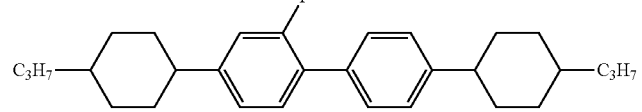 | 4.5 |
| 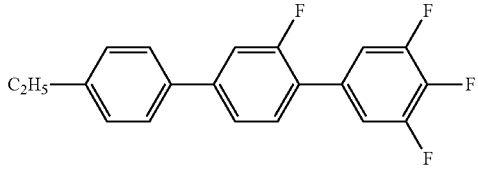 | 9 |

33
-continued

| compound | mass ratio |
|---|---|
| 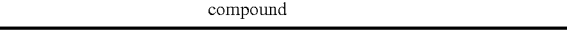 | 9 |

The physical data of the component A are as follows: cp (° C.): 94.9; Δn (20° C., 589 nm): 0.119; $V_{th}$ (V): 1.94; Δ∈ (20° C., KHz): 5.3.

Component B is

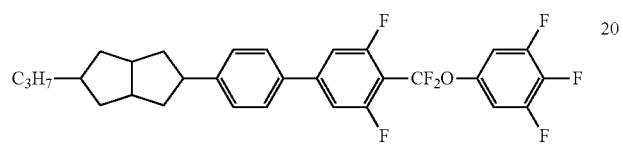

obtained in example 2, and its physical data are as follows: cp (° C.): 91.6; Δn (20° C., 589 nm): 0.119; $V_{th}$ (V): 1.74; Δ∈ (20° C., KHz): 6.4.

From the above data, the use of the compound of formula I can decrease the threshold voltage of the liquid crystal mixture.

Example 31

Liquid Crystal Mixture

The component A and component B were mixed to obtain the liquid crystal mixture. In which the component A consists of the following compounds, which have the following mass ratio:

| compound | mass ratio |
|---|---|
| C₃H₇—[cyclohexyl-cyclohexyl]—CH=CH₂ | 41 |
| C₂H₅—[phenyl-phenyl(F)-phenyl(F,F,F)F] | 10 |
| C₃H₇—[cyclohexyl-cyclohexyl]—CH=CH—CH₃ | 13 |
| H₃C—[phenyl-cyclohexyl-cyclohexyl]—CH=CH₂ | 4 |
| C₃H₇—[phenyl-phenyl(F)-phenyl(F,F,F)F] | 10 |
| H₃C—[phenyl-cyclohexyl-cyclohexyl]—CH₂CH₂CH=CH₂ | 10 |

-continued

| compound | mass ratio |
|---|---|
| 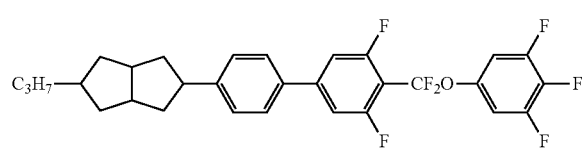 | 6 |
| 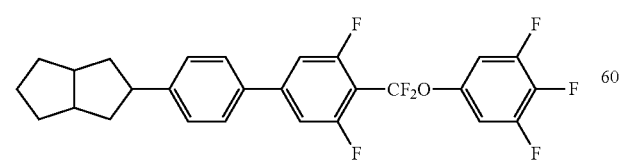 | 6 |

The physical data of the component A are as follows: cp (° C.): 74.6; Δn (20° C., 589 nm): 0.112; $V_{th}$ (V): 1.95; Δ∈ (20° C., KHz): 3.7.

Component B is compounds of formula I obtained in examples:

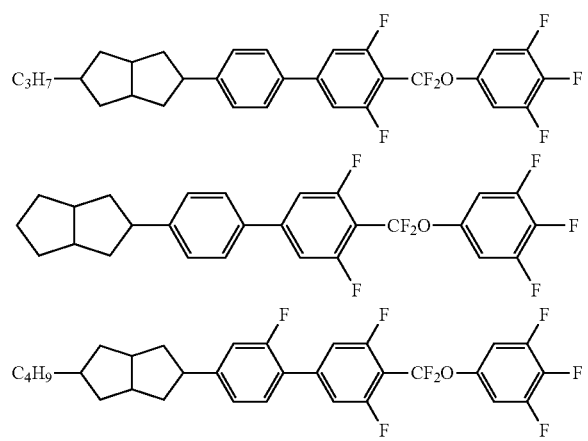

Wherein
the mass ratio of

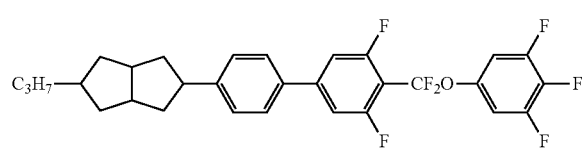

and the component A is 6:100;
the mass ratio of

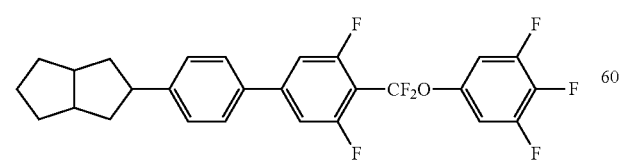

and the component A is 3:100
the mass ratio of

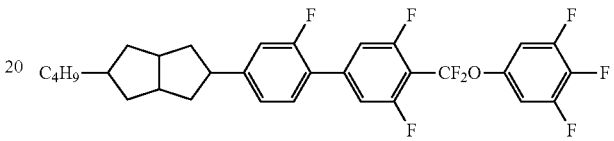

and the component A is 4:100

The physical data of liquid crystal mixture are as follows: cp (° C.): 71.3; Δn (20° C., 589 nm): 0.114; $V_{th}$ (V): 1.65; Δ∈ (20° C., KHz): 4.8.

From the above data, the use of the compound of formula I can decrease the threshold voltage of the liquid crystal mixture.

INDUSTRIAL APPLICATIONS

This invention provides the liquid crystalline compounds of formula I, which have good thermal and UV stability, moderate optical anisotropy (Δn), large positive dielectric anisotropy (Δ∈), and a wide range of nematic phase temperature. It is well suited for development of the liquid crystal mixtures, which have a lower threshold voltage to achieve the quick response. Therefore, it is found that the compounds of formula I and the mixtures comprising compounds of formula I are suitable for a liquid crystal display device, and particularly suitable for liquid crystal display devices, such as TN-TFT, STN, IPS, VA modes.

The invention claimed is:
1. A compound according to formula I:

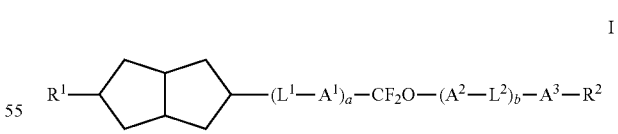

In which, $R^1$ and $R^2$ are selected from at least one of:
H, Cl, F, CN, OCN, OCF$_3$, CF$_3$, CHF$_2$, OCHF$_2$, SCN, NCS, SF$_5$, and alkyl having 1 to 10 carbons, fluorinated alkyl having 1 to 10 carbons, chlorinated alkyl having 1 to 10 carbons, alkoxy having 1 to 10 carbons, fluorinated alkoxy having 1 to 10 carbons, and chlorinated alkoxy having 1 to 10 carbons, wherein one or more —CH$_2$— independently of one another are replaced by one or more of —CH=CH—, —C≡C—, —COO—, —OOC—, —O— and

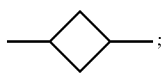

$A^1$, $A^2$ and $A^3$ are independent of one another, and are selected from:

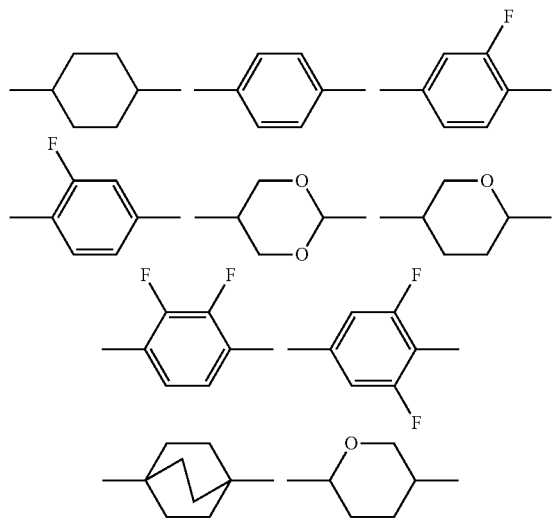

$L^1$ and $L^2$ are independent of one another, and are at least one selected from:

a single bond, —CH=CH—, —C≡C—, —COO—, —OOC—, —CF$_2$O—, —OCH$_2$—, —CH$_2$O—, —OCF$_2$—, —CH$_2$CH$_2$—, —CF$_2$CH$_2$—, —CH$_2$CF$_2$—, —C$_2$F$_4$—, —CF=CF— and —(CH$_2$)$_4$—;

a and b are any integers selected from 0 to 3, and a+b≤4; when a and b are either one of 2 or 3, in the group $A^1$-$L^1$, $A^1$ may be identical or different; $L^1$ may be identical or different; in the group $A^2$-$L^2$, $A^2$ may be identical or different; $L^2$ may be identical or different.

2. A compound according to claim 1, wherein the compound of formula I is according to formula Ia

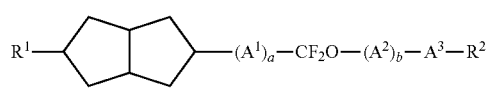

wherein $R^1$, $R^2$, $A^1$, $A^2$, $A^3$, a and b are as defined in claim 1.

3. A compound according to claim 2, wherein the compound of formula I is at least one compound of the formula I1 to I11:

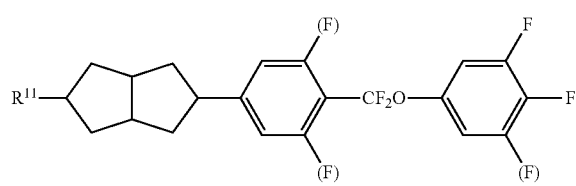

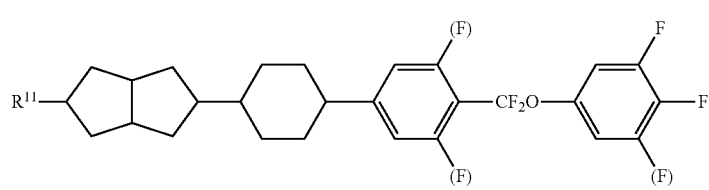

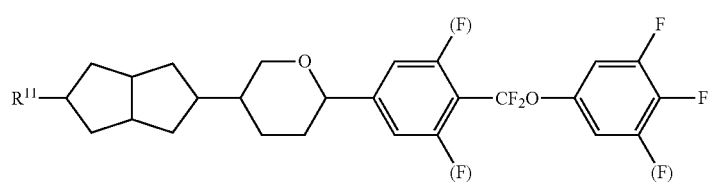

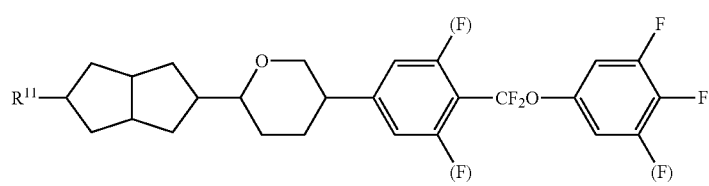

-continued

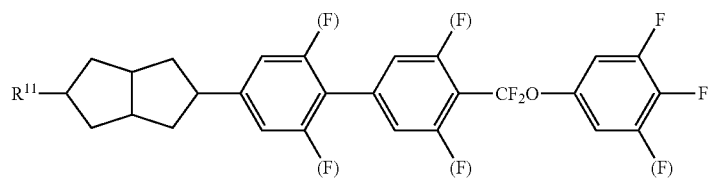
I5

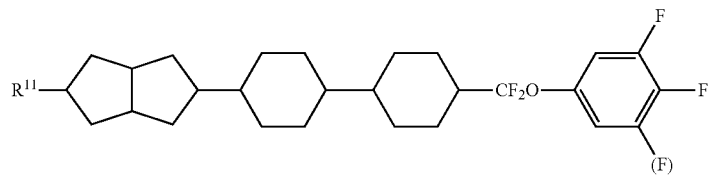
I6

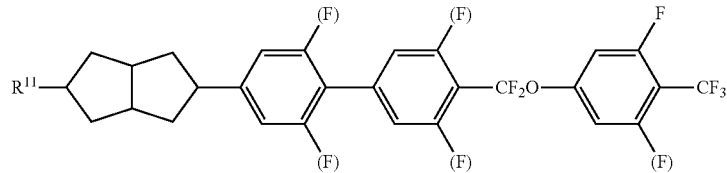
I7

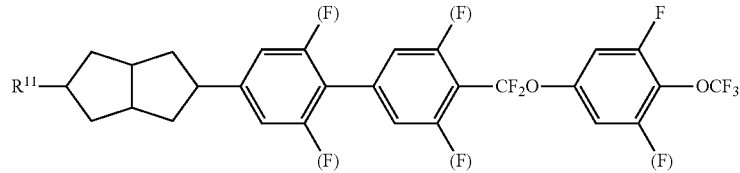
I8

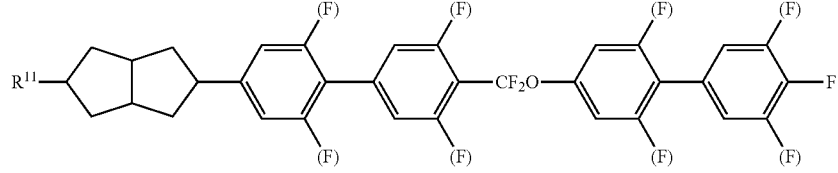
I9

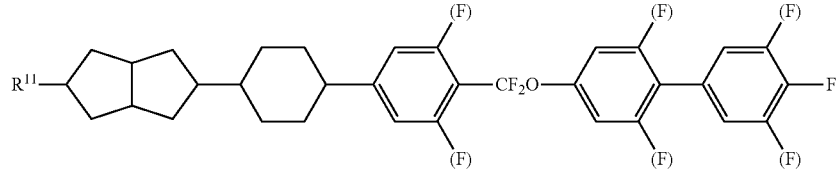
I10

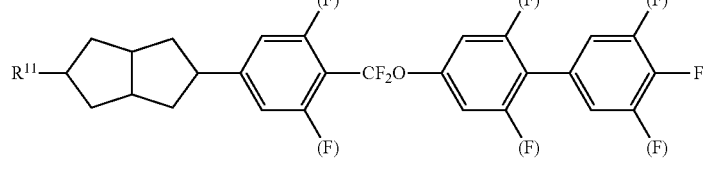
I11 wherein formula I1 to formula I11, $R^{11}$ is at least one selected from the group consisting of H, alkyl having 1 to 10 carbons; alkoxy having 1 to 10 carbons; and wherein (F) represents one of a fluoride substitution or a hydrogen atom on the benzene ring.

4. A liquid-crystal mixture comprising component A, wherein said component A comprises at least one compound selected from compounds of formula I indicated in claim 1.

5. A liquid crystal mixtures according to claim 4, wherein the component A comprises 1-5 compounds of formula I.

6. A liquid crystal mixtures according to claim 5, wherein the component A comprises 1-3 compounds of formula I.

7. A liquid-crystal mixtures according to claim 4, wherein the liquid crystal mixture further comprises component B, wherein component B comprises at least one compound selected from the following formula II to XIV:

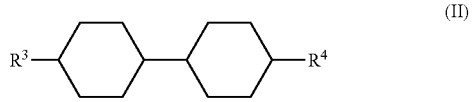
(II)

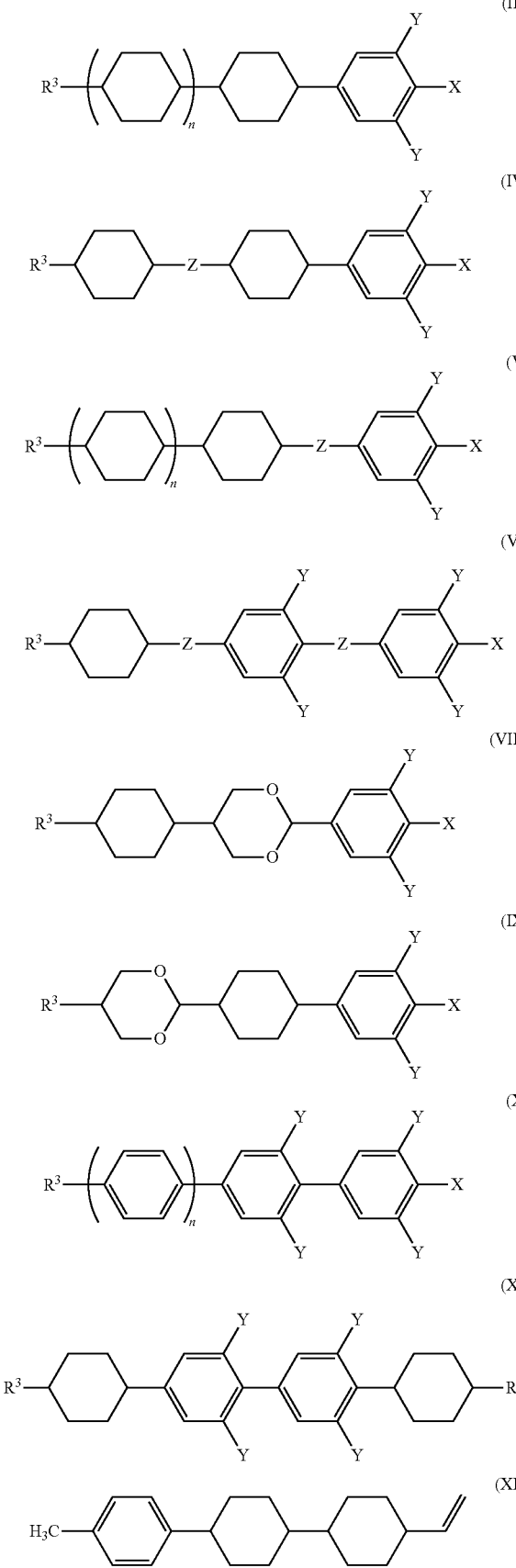

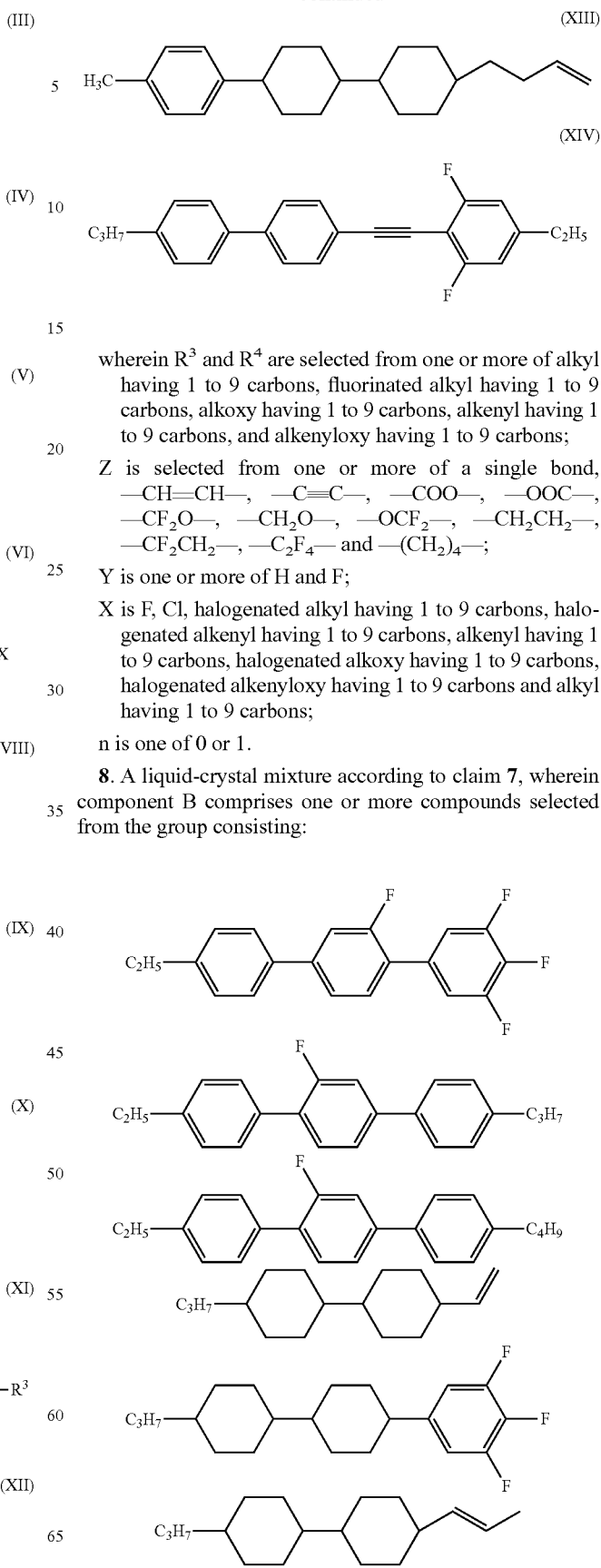

wherein $R^3$ and $R^4$ are selected from one or more of alkyl having 1 to 9 carbons, fluorinated alkyl having 1 to 9 carbons, alkoxy having 1 to 9 carbons, alkenyl having 1 to 9 carbons, and alkenyloxy having 1 to 9 carbons;

Z is selected from one or more of a single bond, —CH=CH—, —C≡C—, —COO—, —OOC—, —CF$_2$O—, —CH$_2$O—, —OCF$_2$—, —CH$_2$CH$_2$—, —CF$_2$CH$_2$—, —C$_2$F$_4$— and —(CH$_2$)$_4$—;

Y is one or more of H and F;

X is F, Cl, halogenated alkyl having 1 to 9 carbons, halogenated alkenyl having 1 to 9 carbons, alkenyl having 1 to 9 carbons, halogenated alkoxy having 1 to 9 carbons, halogenated alkenyloxy having 1 to 9 carbons and alkyl having 1 to 9 carbons;

n is one of 0 or 1.

8. A liquid-crystal mixture according to claim 7, wherein component B comprises one or more compounds selected from the group consisting:

-continued

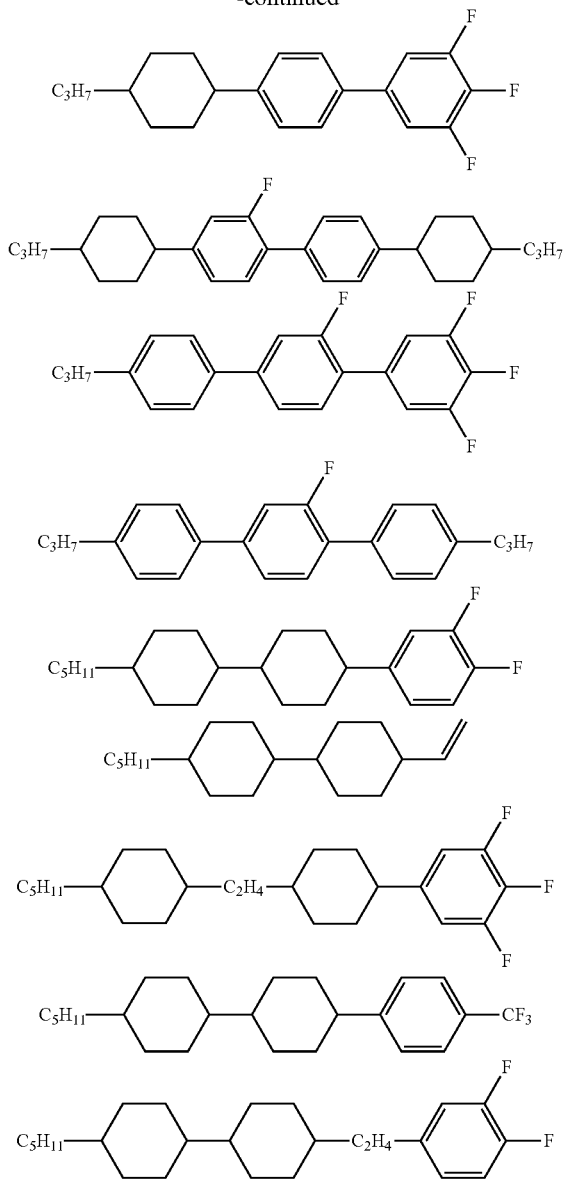

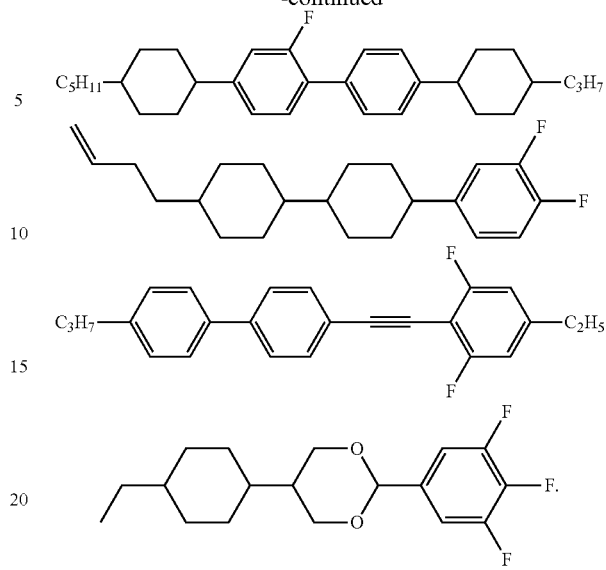

9. A liquid-crystal mixtures according to claim 7, wherein the mass ratio of component A and component B in the liquid-crystal mixtures is 1-70:100.

10. A liquid-crystal mixtures according to claim 7, wherein the mass ratio of component A and component B in the liquid-crystal mixtures is 2-40:100.

11. A liquid-crystal mixtures according to claim 7, wherein the mass ratio of component A and component B in the liquid-crystal mixtures is 13:100.

12. A liquid crystal mixture according to claim 4, wherein the liquid crystal mixtures comprising mixtures a and b, wherein the a mixture comprises components A and B, wherein the component A is

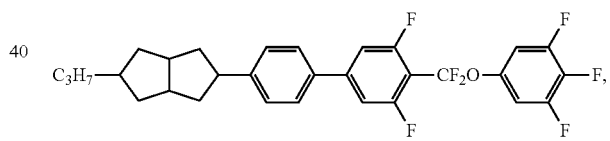

and the component B comprising the following compounds in which the compounds have the following mass ratio:

| compound | mass ratio |
| --- | --- |
| 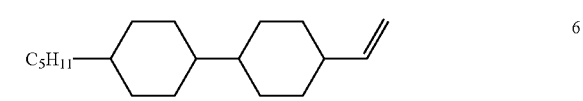 | 21 |
| 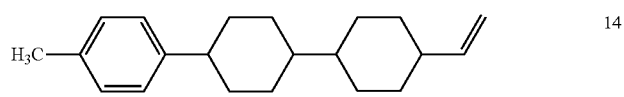 | 6 |
|  | 14 |

| compound | mass ratio |
|---|---|
| C₃H₇—[Cy]—[Cy]—[Ph(3,4,5-F)] | 6 |
| C₃H₇—[Cy]—[Ph]—[Ph(3,4,5-F)] | 16 |
| H₃C—[Ph]—[Cy]—[Cy]—CH₂CH₂CH=CH₂ | 10 |
| C₅H₁₁—[Cy]—[Ph(2-F)]—[Ph]—[Cy]—C₃H₇ | 4.5 |
| C₃H₇—[Cy]—[Ph(2-F)]—[Ph]—[Cy]—C₃H₇ | 4.5 |
| C₂H₅—[Ph]—[Ph(2-F)]—[Ph(3,4,5-F)] | 9 |
| C₃H₇—[Ph]—[Ph(2-F)]—[Ph(3,4,5-F)] | 9 | wherein for the mixture a, the mass ratio of component A and component B is 13:100; and wherein the mixture b comprising the components A and B, wherein the component A comprising at least one of:

C₃H₇—[bicyclopentane]—[Ph]—[Ph(3,5-F)]—CF₂O—[Ph(3,4,5-F)]

C₄H₉—[bicyclopentane]—[Ph(2-F)]—[Ph(3,5-F)]—CF₂O—[Ph(3,4,5-F)]

[bicyclopentane]—[Ph]—[Ph(3,5-F)]—CF₂O—[Ph(3,4,5-F)]

and the component B comprising the following compounds in which the compounds have the following mass ratio:
| compound | mass ratio |
|---|---|
| 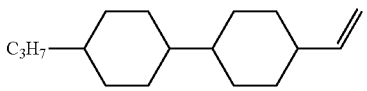 | 41 |
| 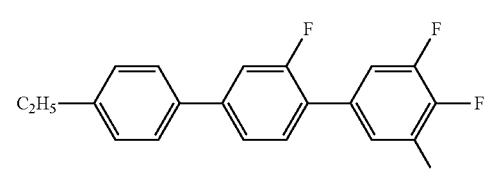 | 10 |
| 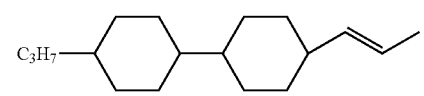 | 13 |
| 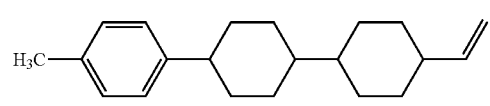 | 4 |
| 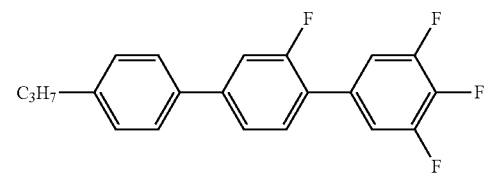 | 10 |
| 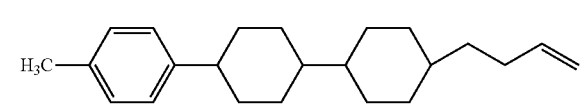 [SMILES: C=CCCC1CCC(C2CCC(c3ccc(C)cc3)CC2)CC1] | 10 |
| 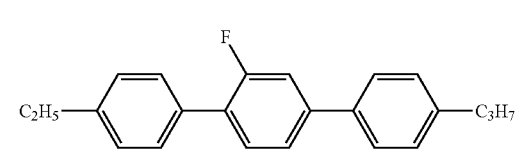 | 6 |
| 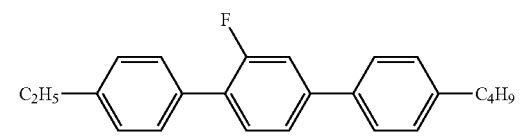 | 6 | wherein said mixture b, the mass ratio of
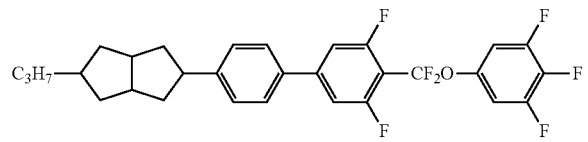
and the component B is 6:100; the mass ratio of
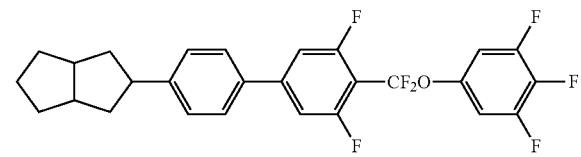
and the component B is 3:100; the mass ratio of
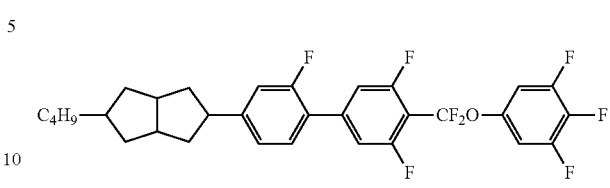
and the component B is 4:100.
13. A liquid crystal display incorporating a liquid crystal compound according to claim 1, wherein the display is one of TN-TFT, STN, IPS and VA liquid crystal displays.
* * * * *